(12) United States Patent
Kitagawa et al.

(10) Patent No.: US 6,379,552 B1
(45) Date of Patent: Apr. 30, 2002

(54) METHOD FOR RESOLVING OPTICAL ISOMERS

(75) Inventors: Tetsuji Kitagawa; Atsushi Okamoto; Takashi Kanai; Katsuhiro Shibayama; Tomoyuki Aoki; Shinobu Yamakawa, all of Aichi (JP)

(73) Assignee: Toray Industries, Inc. (JP)

( * ) Notice: Subject to any disclaimer, the term of this patent is extended or adjusted under 35 U.S.C. 154(b) by 0 days.

(21) Appl. No.: 09/347,062

(22) Filed: Jul. 2, 1999

(30) Foreign Application Priority Data

| Jul. 6, 1998 | (JP) | 10-190593 |
| Sep. 22, 1998 | (JP) | 10-267601 |
| Feb. 5, 1999 | (JP) | 11-028193 |

(51) Int. Cl.$^7$ .......................... B01D 15/00; C07C 69/34
(52) U.S. Cl. .......................... 210/656; 210/660; 203/57; 560/226
(58) Field of Search .......................... 560/226; 203/57; 210/656, 660

(56) References Cited

U.S. PATENT DOCUMENTS

| 4,874,473 A | | 10/1989 | Arlt |
| 5,498,752 A | * | 3/1996 | Negawa et al. |
| 5,763,645 A | | 6/1998 | Negawa |

FOREIGN PATENT DOCUMENTS

| EP | 0471082 | 2/1992 |
| FR | 2176621 A | 11/1973 |
| FR | 2176621 | 11/1973 |
| FR | 2593409 | 7/1987 |

OTHER PUBLICATIONS

Armstrong, D. W. et al. "Planar chromatographic separation of enantiomers and diastereomers with cyclodextrin mobile phase additives" J. Chromatography, vol. 448, pp. 345–354, 1988.*

* cited by examiner

Primary Examiner—James O. Wilson
Assistant Examiner—Leigh C. Maier
(74) Attorney, Agent, or Firm—Schnader Harrison Segal & Lewis LLP

(57) ABSTRACT

A method for efficiently resolving optical isomers, in which a discriminating liquid consisting of a discriminating agent capable of discriminating optical isomers and a diluent are brought into contact with a mixture containing said optical isomers in countercurrent flow, to resolve the optical isomers by adsorption separation, distillation separation, absorption separation or membrane separation, and recovered at an optical isomer content of 5 wt % or less for recycled use, under one or more of the following conditions:

(a) the dielectric constant of the diluent is 30 or less and the viscosity of the discriminating liquid is 0.2 Pa·s or less at the temperature of the resolving operation;

(b) the discriminating agent contained has the effect of splitting the $^1$H or $^{13}$C-NMR spectrum peak of the optical isomers when added and the diluent contained has a dielectric constant equal to or lower than the dielectric constant of the measuring solvent at the time of measuring the $^1$H or $^{13}$C-NMR spectrum;

(c) the boiling point of at least one compound of the discriminating agent at the pressure of the resolving operation is higher than the boiling point of at least one compound of the diluent at the pressure of the resolving operation;

(d) the boiling point of at least one compound of the diluent at the pressure of the resolving operation is higher than the boiling point of the optical isomers to be resolved, at the pressure of the resolving operation, by 10° C. or more; and (e) the concentration of the discriminating agent in the discriminating liquid is 10 wt % or more.

27 Claims, 3 Drawing Sheets

METHOD FOR RESOLVING OPTICAL ISOMERS

BACKGROUND OF THE INVENTION

The present invention relates to a method for resolving optical isomers.

Optical antipodes obtained by optical resolution are widely used as various chemical products, for example, as agricultural chemicals, drugs, food additives and their intermediates.

Optical antipodes include optically active halogen-containing compounds, amino acids, amino acid derivatives, carboxylic acids, carboxylic acid derivatives, amine-containing compounds, alcohol compounds, hydroxycarboxylic acids, hydroxycarboxylic acid derivatives, etc.

Long-established methods for obtaining optical antipodes from optical isomers by optical resolution include preferential precipitation methods, diastereomeric salt precipitation methods, etc. (Kikan Kagaku Sosetsu, Separation of Optical Isomers (in Japanese), No. 6, 1989, Gakkai Shuppan Center).

In addition to the above methods, various optical resolution methods are proposed. For example, optical resolution methods by liquid chromatography (adsorption separation), optical resolution methods using any separation membrane for optical resolution with an optically active source immobilized in a membrane, etc. are available.

In the adsorption separation of optical isomers, adsorption separation using an adsorbent with an optically active source immobilized is widely known. For example, known adsorbents for adsorption separation of optical isomers include polysaccharide derivatives (esters of cellulose, amylose, etc., carbamates, etc.), carried or not carried by silica gel, cyclodextrin derivatives, carried or not carried by silica gel, etc., polyacrylate derivatives carried or not carried by silica gel, etc. Adsorption separation of optical isomers by use of polysaccharide derivatives is reported by Yajima and Okamoto (Bull. Chem. Soc. Jpn., 68, 3289–3307 (1995). Furthermore, a method for resolving optical isomers using, an adsorbent and a mobile phase containing an optical antipode with a structure similar to that of the optical isomers to be resolved is disclosed in FR2593409.

For distillation separation of optical isomers, a resolution method by extractive distillation is disclosed in FR2176621A. Furthermore, HU212256B discloses a method for resolving amphetamine-enantioisomers by fractional distillation.

Moreover, compounds similar or identical to cyclodextrin derivatives used as discriminating agents in the present invention are disclosed in EP407412B and US4948395 as compounds of a stationary phase for optical isomer resolution.

One compound (optical antipode) can be removed from of optical isomers by various methods as described above. However, since the needs for resolving optical isomers are not perfectly satisfied by these known methods, a new resolution method is being demanded. Since preferential precipitation methods and diastereomeric salt precipitation methods need a solid-liquid separation step, they must be carried out as a batch process causing such problems as low productivity and complicated operation.

In the conventional adsorption separation methods for optical isomers, as can be seen typically from adsorbents having a polysaccharide derivative, etc. carried by silica gel, the adsorbents have generally low mechanical strength, and it is difficult to use them in an industrial separation process. Furthermore, these adsorbents are very expensive since they are produced in long processes, and moreover since they have a polysaccharide derivative simply carried, the polysaccharide derivative is disadvantageously eventually dissolved out. In the case of the resolution method using a mobile phase containing an optical antipode disclosed in FR2593409, etc., any device for recycling the mobile phase desirable in industrial separation and the requirements necessary for efficient industrial production are not referred to.

As a conventional distillation separation method for optical isomers, a resolution method by extractive distribution separation is disclosed in FR2176621A. The invention presents an idea concerning the resolution of optical isomers by use of an extracting agent, but it leaves many problems to be solved such as the recycling of the extracting agent and the selection of an optimum extracting agent. HU212256B discloses a resolution method for amphetamine.enantioisomers by fractional distillation. In the invention, a specific resolving agent and amphetamine isomers to be resolved are homogenized, to obtain a specific optical antipode by fractional distillation, but since the homogenization step (for example, a diastereomeric clathrate compound is preferentially precipitated) is necessary, no continuous highly productive process can be performed.

Moreover, since there is no one adsorption separating agent which can separate all of many optical isomers, the development of various new adsorption separating agents and separation systems is desired.

A new optical resolution method which can solve these various problems is demanded and is an object of this invention.

SUMMARY OF THE INVENTION

We have found that optical isomers can be efficiently resolved by a method for in which a discriminating liquid, comprising a discriminating agent capable of discriminating optical isomers and a diluent, is brought into contact with a mixture containing the optical isomers in counter current flow, and to resolve the optical isomers by adsorption separation, distillation separation, absorption separation or membrane separation. The discriminating liquid is recycled at an optical isomer content of 5 wt % or less. One or more of the following conditions is present in the resolving step:

(a) The dielectric constant of the diluent is 30 or less and the viscosity of the discriminating liquid is 0.2 Pa·s or less at the temperature of the resolving operation.

(b) The discriminating agent has the property of splitting the $^1$H or $^{13}$C-NMR spectrum peak of the optical isomers and the diluent has a dielectric constant equal to or lower than the dielectric constant of the measuring solvent at the time of measuring the $^1$H or $^{13}$C-NMR spectrum.

(c) The boiling point of at least one compound of the discriminating agent, at the pressure of the resolving operation is higher than the boiling point of at least one compound of the diluent at the pressure of the resolving operation.

(d) The boiling point of at least one compound of the diluent at the pressure of the resolving operation is higher by 10° C. or more than the boiling point of the optical isomers to be resolved, at the pressure of the resolving operation (e) The concentration of the discriminating agent in the discriminating liquid is 10 wt % or more.

DESIRABLE EMBODIMENTS

Figure 1:
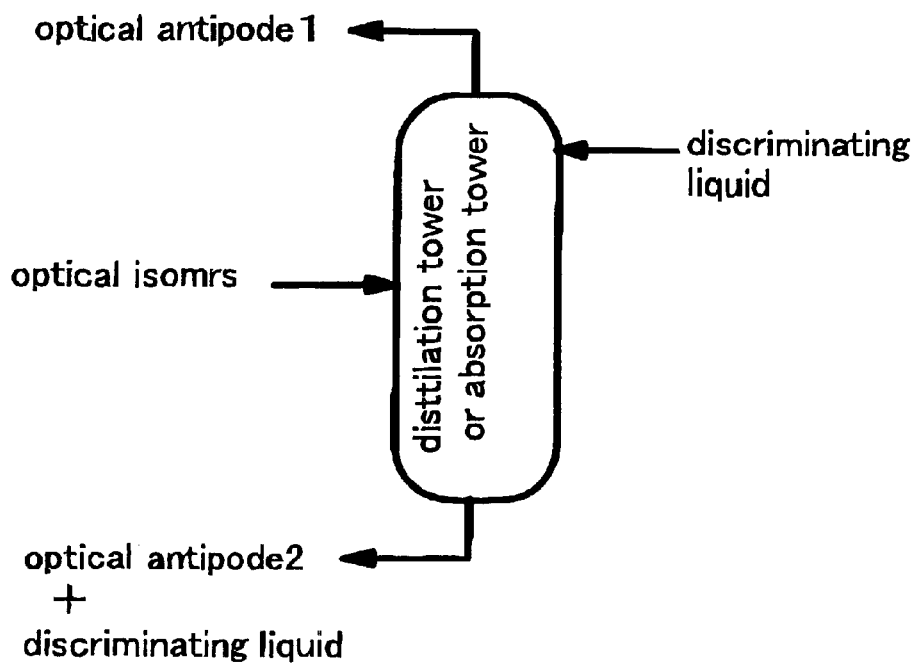
FIG. 1 shows the flow paths in a distillation separator of the present invention.

In this invention the expression "optical isomers" refers to a mixture of isomers as plural optical antipodes, and the expression "optical antipode" refers to one optically active compound.

Preferable optical isomers in the present invention include amino acids, amines, carboxylic acids, hydroxycarboxylic acids, hydrocarbons, halogenated hydrocarbons, ketones, alcohols, ethers and their derivatives. Amine derivatives, carboxylic acid derivatives, halogenated hydrocarbons, ketones and ethers are more preferable. Carboxylic acid derivatives, halogenated hydrocarbons, ketones and ethers are especially preferable.

The carboxylic acid derivatives as optical isomers in the present invention include, for example, methyl 2-chloropropionate, ethyl 2-chloropropionate, methyl 2-bromopropionate, ethyl 2-bromopropionate, pentyl 2-bromopropionate, sec-butyl 2-bromopropionate, sec-hexyl 2-bromopropionate, α-acetyl-α-methyl-γ-butyrolactone, β-butyrolactone, etc.

The halogenated hydrocarbons include 3-bromo-1-butene, 1-chloro-2-bromopropane, 2,3-dichlorobutane, 1,2-dichloropropane, etc. The ketones include 3-chloro-2-butanone, 2-chloro-cyclopentanone, 2-chloro-cyclohexanone, etc.

The ethers include 2-bromomethyl-tetrahydrofuran, butadiene-monoepoxide, 2-chloromethyl-tetrahydrofuran, 3,4-dihydro-2-methoxypyran, trans-2,5-dimethoxytetrahydrofuran, epichlorohydrin, epibromohydrin, etc. However, the optical isomers are not limited to them.

The expression "discriminating liquid" in the present invention refers to a liquid obtained by diluting a discriminating agent by use of a diluent, and is used especially for resolving optical isomers by adsorption separation, distillation separation, absorption separation or membrane separation in an industrial optical resolution process.

The discriminating liquid in the present invention is used for resolution by adsorption separation, distillation separation, absorption separation or membrane separation. Resolution by adsorption separation or distillation separation is preferable, and resolution by distillation separation is especially preferable.

The expression "countercurrent contact " in the present invention means that the flow of the discriminating liquid and the flow of the optical isomers to be resolved are brought into contact with each other in countercurrent flow in a process system. A moving bed process or simulated moving bed process for adsorption separation, an extractive distillation process for distillation separation, and an ordinary absorption separation process, etc. are themselves known.

The resolution by adsorption separation in the present invention uses a solid-liquid equilibrium. In this method, from the discriminating liquid containing dissolved optical isomers, i.e., from a mobile phase, the optical antipode less amenable to be discriminated by the discriminating agent is preferentially adsorbed by an adsorbing phase by adsorption separation etc., for separation from the optical antipode likely more amenable to be discriminated by the discriminating agent, and to remain in the mobile phase (the optical antipode caught in the discriminating liquid). The resolution method by adsorption separation can comprise any method for solid-liquid contact, but the resolution by use of a simulated moving bed with countercurrent contact is especially preferable as the process.

The resolution by distillation separation or absorption separation in the present invention uses a gas-liquid equilibrium. In this method, from the discriminating liquid containing dissolved optical isomers, the optical antipode that is less amenable to be discriminated by the discriminating agent is preferentially removed by distillation or absorption, for separation from the antipode that is more amenable to be discriminated (the antipode taken into the discriminating liquid). The resolution method using distillation separation can be any method as far as gas-liquid contact operation is used, but extractive distillation separation with countercurrent contact is especially preferable.

The resolution of optical isomers by membrane separation in the present invention comprises an optical antipode not amenable to be discriminated by the discriminating agent in the discriminating liquid containing dissolved optical isomers, preferentially removed by membrane separation from the optical antipode amenable to be discriminated (the antipode caught in the discriminating liquid). As for the method of membrane separation, it is especially preferable that the membrane consists of plural layers, and that the discriminating liquid and the optical isomers to be separated are brought into contact with each other in countercurrent flow.

The discriminating agent in the present invention refers to a compound which can discriminate at least one specific optical antipode of from the optical isomers desired to be resolved. The discriminating agent is only required to be an optically active compound and to be able to discriminate a specific optical antipode. Above all, a discriminating agent consisting of an optically active compound with at least two asymmetric atoms is preferable. Compounds which can be used as the discriminating agent include cyclic host compounds such as saccharides, saccharide derivatives (cyclodextrins, cyclodextrin derivatives, polysaccharides, polysaccharide derivatives, etc.), tartaric acid, tartaric acid derivatives, and optically active crown ethers, natural optically active compounds, derivatives of natural optically active compounds, host compounds in the relation of host-guest compounds, etc. An optically active compound with one or more axially asymmetric portions such as binaphtol is also an optically active compound with two asymmetric atoms in the present invention.

The discriminating agent in the present invention may be a compound in which asymmetric atoms are adjacently bonded to each other. In this case, since an optical isomer discrimination situs is formed between the adjacent asymmetric atoms, the compound acts as a discriminating agent with a high capacity for separability. Furthermore, a derivative obtained by chemically modifying the substituent groups around the adjacent asymmetric atoms is more preferable since its optical isomer discriminatability can be higher.

When the discriminating agent in the discriminating liquid discriminates optical isomers as in the present invention, the use of an optically active compound having at least two asymmetric atoms assures higher resolvability as described above, and the resolution by countercurrent contact assures further higher productivity.

The compounds which can be preferably used as discriminating agents having adjacent asymmetric atoms in the present invention include, for example, saccharides, hydroxycarboxylic acids, saccharide derivatives, hydrocarboxylic acid derivatives, etc. Saccharides and saccharide derivatives are more preferable, and cyclodextrins and cyclodextrin derivatives are especially preferable.

The saccharides in the present-invention include disaccharides, trisaccharides, oligosaccharides, cyclodextrins, polysaccharides, etc.

The cyclodextrin derivatives in the present invention can be any cyclodextrin derivatives modified at the hydroxyl groups of cyclodextrins, and acylated derivatives, etherified derivatives and partially etherified and partially acylated derivatives are especially preferable. Among partially etherified and partially acylated derivatives, a derivative having ether groups at the 2-position and 6-position hydroxyl groups of the glucose unit and an ether group or acyl group at the 3-position hydroxyl group are preferable. Especially, 2,6-O-dialkyl-3-O-acyl-cyclodextrins and 2,3,6-O-trialkyl-cyclodextrins wherein each alkyl group or each acyl group has 1 to 15 carbon atoms, are preferable.

Furthermore, cyclodextrin derivatives mainly consisting of any of the following are preferable: heptakis(2,6-O-dipentyl-3-O-trifluoroacetyl)-β-cyclodextrin, heptakis(2,6-O-dipentyl-3-O-trichloroacetyl)-β-cyclodextrin, heptakis(2,6-O-dipentyl-3-O-butyryl)-β-cyclodextrin, heptakis(2,6-O-dipentyl-3-O-acetyl)-β-cyclodextrin, heptakis(2,6-O-dipentyl-3-O-propanoyl)-β-cyclodextrin, hexakis(2,6-O-dipentyl-3-O-trifluoroacetyl)-α-cyclodextrin, hexakis(2,6-O-dipentyl-3-O-trichloroacetyl)-α-cyclodextrin, hexakis(2,6-O-dipentyl-3-O-butyryl)-α-cyclodextrin, hexakis(2,6-O-dipentyl-3-O-acetyl)-α-cyclodextrin, hexakis(2,6-O-dipentyl-3-O-propanoyl)-α-cyclodextrin, octakis(2,6-O-dipentyl-3-O-trifluoroacetyl)-γ-cyclodextrin, octakis(2,6-O-dipentyl-3-O-trichloroacetyl)-γ-cyclodextrin, octakis(2,6-O-dipentyl-3-O-butyryl)-γ-cyclodextrin, octakis(2,6-O-dipentyl-3-O-acetyl)-γ-cyclodextrin, octakis(2,6-O-dipentyl-3-O-propanoyl)-γ-cyclodextrin, heptakis(2,6-O-dihexyl-3-O-trifluoroacetyl)-β-cyclodextrin, heptakis(2,6-O-diactyl-3-O-trifluoroacetyl)-β-cyclodextrin, heptakis(2,6-O-dioctyl-3-O-acetyl)-β-cyclodextrin, heptakis(2,6-O-dioctyl-3-O-propiohyl)-β-cyclodextrin, heptakis(2,6-O-dioctyl-3-O-butyryl)-β-cyclodextrin, heptakis(2,6-O-dioctyl-3-O-valeryl)-β-cyclodextrin, heptakis(2,6-O-dioctyl-3-O-hexanoyl)-β-cyclodextrin, heptakis(2,6-O-didecyl-3-O-trifluoroacetyl)-β-cyclodextrin, heptakis(2,6-O-dibutyl-3-O-propionyl)-β-cyclodextrin, heptakis(2,6-O-dibutyl-3-O-trifluoroacetyl)-β-cyclodextrin, octakis(2,6-O-dihexyl-3-O-trifluoroacetyl)-γ-cyclodextrin, octakis(2,6-O-dioctyl-3-O-trifluoroacetyl)-γ-cyclodextrin, octakis(2,6-O-dioctyl-3-O-acetyl)-γ-cyclodextrin, cyclodextrin, octakis(2,6-O-dioctyl-3-O-propionyl)-γ-cyclodextrin, octakis(2,6-O-dioctyl-3-O-butyryl)-γ-cyclodextrin,-γ-cyclodextrin, octakis (2,6-O-dioctyl-3-O-valeryl)-γ-cyclodextrin, octakis(2,6-O-dioctyl-3-O-hexanoyl)-γ-cyclodextrin, octakis(2,6-O-didecyl-3-O-trifluoroacetyl)-γ-cyclodextrin, octakis(2,6-O-dibutyl-3-O-propionyl)-γ-cyclodextrin, octakis(2,6-O-dibutyl-3-O-trifluoroacetyl)-γ-cyclodextrin, hexakis(2,6-O-dihexyl-3-O-trifluoroacetyl)-α-cyclodextrin, hexakis(2,6-O-dioctyl-3-O-trifluoroacetyl)-α-cyclodextrin, hexakis(2,6-O-dioctyl-3-O-acetyl)-α-cyclodextrin, hexakis(2,6-O-dioctyl-3-O-propionyl)-α-cyclodextrin, hexakis(2,6-O-dioctyl-3-O-butyryl)-α-cyclodextrin, hexakis(2,6-O-dioctyl-3-O-valeryl)-α-cyclodextrin, hexakis(2,6-O-dioctyl-3-O-hexanoyl)-α-cyclodextrin, hexakis(2,6-O-didecyl-3-O-trifluoroacetyl)-α-cyclodextrin, hexakis(2,6-O-dibutyl-3-O-propionyl)-α-cyclodextrin, and hexakis(2,6-O-dibutyl-3-O-trifluoroacetyl)-α-cyclodextrin. Cyclodextrin derivatives mainly consisting of any of the following are more preferable: heptakis(2,6-O-dipentyl-3-O-trifluoroacetyl)-β-cyclodextrin, heptakis(2,6-O-dipentyl-3-O-trichloroacetyl)-β-cyclodextrin, heptakis(2,6-O-dipentyl-3-O-butyryl)-β-cyclodextrin, heptakis(2,6-O-dipentyl-3-O-acetyl)-β-cyclodextrin, heptakis(2,6-O-dipentyl-3-O-propanoyl)-β-cyclodextrin, heptakis(2,6-O-dihexyl-3-O-trifluoroacetyl)-β-cyclodextrin, heptakis(2,6-O-dioctyl-3-O-trifluoroacetyl)-β-cyclodextrin, heptakis(2,6-O-dioctyl-3-O-acetyl)-β-cyclodextrin, heptakis(2,6-O-dioctyl-3-O-propionyl)-β-cyclodextrin, heptakis(2,6-O-dioctyl-3-O-butyryl)-β-cyclodextrin, heptakis(2,6-O-dioctyl-3-O-valeryl)-β-cyclodextrin, heptakis(2,6-O-dioctyl-3-O-hexanoyl)-β-cyclodextrin, heptakis(2,6-O-didecyl-3-O-trifluoroacetyl)-β-cyclodextrin, heptakis(2,6-O-dibutyl-3-O-propionyl)-β-cyclodextrin, heptakis(2,6-O-dibutyl-3-O-trifluoroacetyl)-β-cyclodextrin, and octakis(2,6-O-dihexyl-3-O-trifluoroacetyl)-γ-cyclodextrin. Cyclodextrin derivatives mainly consisting of any of the following are especially preferable: heptakis(2,6-O-dihexyl-3-O-trifluoroacetyl)-β-cyclodextrin, heptakis(2,6-O-dioctyl-3-O-trifluoroacetyl)-β-cyclodextrin, heptakis(2,6-O-dioctyl-3-O-acetyl)-β-cyclodextrin, heptakis(2,6-O-dioctyl-3-O-propionyl)-β-cyclodextrin, heptakis(2,6-O-dioctyl-3-O-butyryl)-β-cyclodextrin, heptakis(2,6-O-dioctyl-3-O-valeryl)-β-cyclodextrin, heptakis(2,6-O-dioctyl-3-O-hexanoyl)-β-cyclodextrin, heptakis(2,6-O-didecyl-3-O-trifluoroacetyl)-β-cyclodextrin, heptakis(2,6-O-dibutyl-3-O-propionyl)-β-cyclodextrin, heptakis(2,6-O-dibutyl-3-O-trifluoroacetyl)-β-cyclodextrin, and octakis(2,6-O-dihexyl-3-O-trifluoroacetyl)-γ-cyclodextrin. The especially preferable cyclodextrin derivatives enumerated above mainly consist of any of the compounds represented by the following formula (I) respectively.

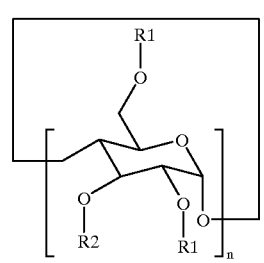

(I)

$n=6-8$
(If R1 denotes n-hexyl, R2 denotes trifluoroacetyl;
if R1 denotes n-octyl, R2 denotes trifluoroacetyl, acetyl, propionyl, butyryl, valeryl or hexanoyl;
if R1 denotes n-decyl, R2 denotes trifluoroacetyl; and
if R1 denotes n-butyl, R2 denotes propionyl or trifluoroacetyl)

Any of the above cyclodextrin derivatives can be synthesized as described below. Cyclodextrin is dissolved into dimethyl sulfoxide (DMSO) solvent, and granular or powdery sodium hydroxide is mixed with the solution. Then, while the exothermic reaction is controlled, an alkyl halide is added dropwise to 1 g of the cyclodextrin at a rate of 5 g/min or less, preferably 1 g/min or less, and after completion of dropwise addition, reaction is effected in a reaction temperature range of 0 to 150° C., preferably 40 to 100° C. for 1 hour or more, for etherification. The etherification product is esterified by an esterifying agent, to produce a cyclodextrin derivative. It is preferable that the halogen of the alkyl halide is chlorine, bromine or iodine. Bromine is more preferable.

It is preferable to use a carboxylic anhydride as the esterifying agent, and in this case, it is preferable to remove the by produced carboxylic acid by distillation. The removed carboxylic acid can be converted into the corresponding carboxylic anhydride by dehydration treatment, etc., to be reused for reaction. Furthermore, since the carboxylic acid is removed before neutralization and water washing, the amount of waste water caused by treatment can be decreased.

The discriminating liquid in the present invention contains an afore said discriminating agent plus a diluent. The diluent should be able to sufficiently dissolve the discriminating agent and should be as low as possible in dielectric constant to such an extent that the discriminatability of the discriminating agent is not impaired, and also should have a low viscosity.

If the diluent in the present invention is a compound with having a large polarity, the molecular interaction between the discriminating agent and the optical isomers is inhibited, lowering the discriminatability, i.e., optical resolvability. So, it is preferable that the dielectric constant of the diluent is 30 or less. More preferable is 10 or less. Diluents having a dielectric constant of 30 or less include, for example, aliphatic hydrocarbon compounds such as dichloromethane, chloroform, 1,1,1-trichloroethane, a-pinene, d-limonene, benzene, toluene, anisole, methylanisole, veratrol, cymene, diethylbenzene, tetralin, dichlorotoluene, chloro-p-xylene, benzotrichloride, n-hexane, petroleum ether, n-decane, n-paraffin, branched paraffin, and olefins, ether compounds such as diethyl ether, and diisopropyl ether, etc., though not limited to them.

The expression "dielectric constant" in the present invention refers to the value obtained by dividing the electrostatic capacity measured with a solvent inserted between the electrode plates of the capacitor of a dielectric constant measuring instrument, by the electrostatic capacity in vacuum. In general when the solvent has larger polarity, the dielectric constant becomes larger. The method for measuring the dielectric constant is described in detail in "New Edition, Handbook on Electrochemistry (in Japanese)" (Denki Kagaku Kyokai, Maruzen K. K., p. 269). As the dielectric constants of the desorbents in the present invention, the values stated in "Third Revision, Basic Part II of Handbook on Chemistry (in Japanese)" (Nihon Kagaku Kyokai, Maruzen K.K., p. 501) and "New Edition, Pocketbook on Solvents (in Japanese)" (Yuki Gosei Kagaku Kyokai, Ohm) can be used.

The diluent in the present invention acts to dilute the discriminating agent for lowering the viscosity of the discriminating liquid. Discriminating agents are generally solids or consistent liquids. The addition of a diluent lowers the viscosity of the discriminating liquid, to allow its use without suffering any pressure loss in the process. Furthermore if the discriminating agent and the diluent are used in recycling after resolution of optical isomers, the lower viscosity of the discriminating liquid assures good operation convenience. In the resolution method of the present invention, if the discriminating liquid which has been used for resolving optical isomers is recovered with the optical isomer content kept at 5 wt % or less, the lowering of purity by contamination in recycled use and the lowering of resolvability can be inhibited. It is preferable that the optical isomer content at the time of recovery of the discriminating liquid in the present invention is 5 wt % or less. More preferable is 3 wt % or less, and further more preferable is 1% or less. Especially preferable is 0.5 wt % or less.

The present invention relates to a method for resolving optical isomers, in which an discriminating liquid comprising an discriminating agent capable of discriminating optical isomers and a diluent is brought into contact with a mixture containing said optical isomers in countercurrent flow, to resolve the optical isomers by adsorption separation, or distillation separation,or absorption separation or membrane separation, and is recovered at an optical isomer content of 5 wt % or less for recycled use, and the discriminating liquid must satisfy one or more of the following conditions:

(a) The dielectric constant of the diluent is 30 or less and the viscosity of the discriminating liquid is 0.2 Pa·s or less at the temperature of the resolving operation.

(b) The discriminating agent has the property of splitting the $^1$H or $^{13}$C-NMR spectrum peak of the optical isomer when added, and the diluent has a dielectric constant equal to or lower than the dielectric constant of the measuring solvent at the time of measuring the $^1$H or $^{13}$C-NMR spectrum.

(c) The boiling point of at least one compound of the discriminating agent at the pressure of the resolving operation is higher than the boiling point of at least one compound of the diluent at the pressure of the resolving operation.

(d) The boiling point of at least one compound of the diluent at the pressure of the resolving operation is higher by 10° C. or more than the boiling point of the optical isomers to be resolved, at the pressure of resolving operation.

(e) The concentration of the discriminating agent in the discriminating liquid is 10 wt % or more.

The above conditions are further described below.

(a) The dielectric constant of the diluent is 30 or less and the viscosity of the discriminating liquid is 0.2 Pa·s or less at the temperature of the resolving operation.

It is important that the discriminating liquid should retain its discriminatability for resolving optical isomers, and shall have sufficient flowability to allow the circulation in the process and recovery as a liquid.

It was found that if a compound having large polarity is used as the diluent, the molecular interaction between the discriminating agent and the optical isomers is inhibited, to which lowers the discriminatability, i.e., optical resolvability. So, it is preferable that the dielectric constant of the diluent is 30 or less. More preferable is 10 or less.

It was also found that if the viscosity of the discriminating liquid is controlled, the handling of the discriminating liquid in the process and the recovery (purification) by distillation or evaporation, etc. can be carried out easily. That is, it is preferable that the viscosity of the discriminating liquid is 0.2 Pa·s (200 cp) or less at the temperature of the resolving operation. More preferable is 0.1 Pa·s (100 cp) or less, and especially preferable is 0.05 Pa·s (50 cp) or less.

In this case, the discrimination of optical isomers by the discriminating agent in a solution is very advantageous for the process of the present invention including resolution and recycling. The reasons are that the optical resolvability in a solution allows (1) continuous operation, hence establishment of a highly productive process, and that the relatively low viscosity of the discriminating liquid allows (2) recovery of the discriminating liquid by such a simple method as distillation or evaporation, to allow recycled use. The resolution method of the present invention is beneficial since the discriminating liquid containing 5 wt % or less of an optical isomers is recovered after resolution of optical isomers, the lowering of purity by contamination in recycled use can be inhibited. It was found that if the condition in the present invention is satisfied, the discriminating liquid can be easily recovered and purified.

The viscosity of the discriminating liquid can be measured by an ordinary method, for example, using an Ubbellohde viscometer.

(b) The discriminating agent contained has the property of splitting the $^1$H or $^{13}$C-NMR spectrum peak of the optical isomers when added and the diluent contained has a dielectric constant equal to or lower than the dielectric constant of the measuring solvent at the time of measuring the $^1$H or $^{13}$C-NMR spectrum.

In the present invention, it is preferable that the discriminating agent has the property of splitting the $^1$H or $^{13}$C-NMR spectrum peak of the optical isomers when added. Usually optical isomers such as R-isomer, S-isomer and racemic modification are equal in $^1$H or $^{13}$C-NMR spectrum peak. The splitting of the peak in the present invention is caused by any difference in the intensity of the molecular interaction between the discriminating agent and each of the optical isomers. The effect that the $^1$H or $^{13}$C-NMR spectrum peak of optical isomers is split by adding a discriminating agent essentially suggests that the discriminating agent discriminates the optical isomers. In the present invention, owing to the state of a solution, resolution is possible since the relative differences in discriminatability between the discriminating agent and respective optical isomers are large, even though the molecular interactions between them are relatively weak.

In this case, the discrimination of optical isomers by the discriminating agent in a solution is very advantageous for the process of present invention, including resolution and recycling. The reasons are (1) that the optical resolution in a solution allows continuous operation, hence establishment of a highly productive process, and (2) that the relatively weak interactions between the optical isomers and the discriminating liquid in a solution allow the discriminating liquid to be recovered by such a simple method as distillation or evaporation, to allow recycled use. In the resolution method of the present invention, unless the optical isomers content of the discriminating liquid recovered after resolving the optical isomers is 5 wt % or less, the purity is lowered by contamination in recycled use. However, it was found that according to the method of the present invention, the discriminating agent can be easily recovered and purified for the reason stated above.

It is preferable that the $^1$H or $^{13}$C-NMR spectrum in the present invention is measured using a measuring instrument with an observation frequency of 200 MHz or more. It is most preferable to use an instrument of 500 MHz or more. The reason is that if the observation frequency is low, the spectrum resolving power becomes low, and therefore that the splitting of the peak to be observed may be overlooked. The $^1$H or $^{13}$C-NMR spectrum in the present invention is measured according to any established method.

The solvents which can be used as the measuring solvent in the present invention are those usually used for NMR testing and include, for example, heavy chloroform ($CDCl_3$), heavy dichloromethane ($CD_2Cl_2$), heavy benzene ($C_6D_6$) heavy DMSO, heavy water, heavy toluene ($CD_3C_6D_6$), heavy methanol ($CD_3OD$, $CD_3OH$), etc.

It is preferable that the dielectric constant of the diluent in the present invention is equal to or lower than the dielectric constant of the measuring solvent used for confirming the splitting of the peak in the $^1$H or $^{13}$C-NMR spectrum.

The reason is that since the diluent with a dielectric constant as specified above is considered to be small in the interaction with the discriminating agent, the discriminatability of the discriminating agent can be sufficiently manifested.

(c) The boiling point of at least one compound of the discriminating agent at the pressure of the resolving operation is higher than the boiling point of at least one compound of the diluent at the pressure of the resolving operation.

In the present invention, it is preferable that the boiling point of at least one component of the discriminating agent at the pressure of the resolving operation is higher than the boiling point of at least one component of the diluent at the pressure of the resolving operation. It is preferable that the difference in boiling point is 10° C. or more. More preferable is 20° C. or more, and especially preferable is 30° C. or more. The reason is that if the boiling point of the discriminating agent is higher than the boiling point of the diluent, the discriminating agent can be easily separated and purified by distillation and/or evaporation in recycled use. If the diluent consists of plural components, it is only required that at least one component satisfies the above condition.

(d) The boiling point of at least one compound of the diluent at the pressure of the resolving operation is higher than the boiling point of the optical isomers to be resolved, at the pressure of the resolving operation by 10° C. or more.

In the present invention, it is preferable that the boiling point of at least one component of the diluent at the pressure of resolving operation is higher than the boiling point of the optical isomers to be resolved, at the pressure of the resolving operation by 10° C. or more. It is more preferable that the difference in boiling point is 20° C. or more, and especially preferable is 30° C. or more. The reason is that if the difference between the diluent and the optical isomers in boiling point is 10° C. or more, the discriminating agent can be easily separated and purified by distillation and/or evaporation in recycled use.

In the present invention, it is preferable that the boiling points (°C.) of the respective components satisfy the following relation in the resolving operation.

Boiling point of a component of discriminating agent>Boiling point of a component of diluent>Boiling point of optical isomers+10° C.

If this condition is satisfied, it becomes easier to continuously and efficiently produce optical isomers resolved by the discriminating liquid.

That is, after the optical isomers are brought into contact with the discriminating liquid, they are separated into an optical antipode retained in the discriminating liquid and the other optical antipode passing out of the discriminating liquid without being discriminated by the discriminating agent of the discriminating liquid. The respective optical antipodes can be obtained at higher optical purities. If the process consists of plural steps (if the contact operation is repeated plural times), more highly pure optical antipodes can be obtained. In this case, if the above condition is satisfied, the optical antipode kept in the discriminating liquid can be easily separated by distillation and/or evaporation. Furthermore, even if a slight amount of the diluent flows out with the optical antipode, the discriminating agents is advantageously not lost. The small amount of removed diluent can also be purified by further distillation and/or evaporation.

(e) The concentration of the discriminating agent in the discriminating liquid is 10 wt % or more.

It is preferable that the concentration of the discriminating agent in the discriminating liquid in the present invention is 10 wt % or more. More preferable is 20 wt % or more, and further more preferable is 30 wt % or more. Especially preferable is 40 wt % or more.

It is preferable that the discriminating liquid in the present invention satisfies two or more of the above conditions (a) through (e). Above all, it is preferable to satisfy (a) and (b), or (a) and (c), or (a) and (d), or (a) and (e), or (b) and (c), or (b) and (d), or (b) and (e), or (c) and (d).

It is especially preferable that the discriminating liquid satisfies three or more conditions. Above all, it is preferable to satisfy (a) and (b) and (c), or (a) and (b) and (d), or (a) and (b) and (e), or (a) and (c) and (d), or (a) and (b) and (c) and (d), or (b) and (c) and (d), (c) and (d) and (e), (a) and (c) and (d) and (e), or (b) and (e) and (c) and (d).

Among them, it is preferable to satisfy (c) and (d), and it is especially preferable to satisfy (c) and (d) and any one or more of (a), (b) and (e). It is most preferable to satisfy all of (a) through (e).

If adsorption separation is used in the present invention, it is preferable to satisfy (a) and (c), or (a) and (d), or (a) and (e), or (a) and (b) and (c), or (a) and (b) and (d), or (a) and (b) and (e), or (a) and (c) and (d), or (a) and (b) and (c) and (d), or (b) and (c), or (b) and (d), or (b) and (e), or (b) and (c) and (d), or (c) and (d), or (c) and (d) and (e), or (a) and (c) and (d) and (e), or (b) and (c) and (d) and (e), or (a) and (b) and (c) and (d) and (e). It is more preferable to satisfy (c) and (d), and it is especially preferable to satisfy (c) and (d) and any one or more of (a), (b) and (e).

If distillation separation, absorption separation or membrane separation is used in the present invention, it is preferable to satisfy (a) and (b), or (a) and (c), or (a) and (d), or (a) and (e), or (a) and (b) and (c), or (a) and (b) and (d), or (a) and (b) and (e), or (a) and (c) and (d), or (a) and (b) and (c) and (d), or (b) and (c), or (b) and (d), or (b) and (e), or (b) and (c) and (d), or (c) and (d), or (c) and (d) and (e), or (a) and (c) and (d) and (e), or (b) and (c) and (d) and (e), or (a) and (b) and (c) and (d) and (e). It is more preferable to satisfy (c) and (d), and it is especially preferable to satisfy (c) and (d) and any one or more of (a) and (b) and (e).

In the present invention, when optical isomers are brought into contact with the discriminating liquid, they are separated into an optical antipode retained in the discriminating liquid, being discriminated by the discriminating agent of the discriminating liquid, and the other antipode being removed from the discriminating liquid, without being discriminated by the discriminating agent of the discriminating liquid. The respective optical antipodes can be obtained at higher optical purities. It is preferable that the process consists of plural steps (the contact operation is repeated plural times), since more highly pure optical antipodes can be obtained.

Irrespective of the process in the present invention, the optical antipode dissolved in the discriminating liquid must be separated from it. It is preferable to recycle the separated optical antipode and the discriminating liquid respectively as required into the process system. A preferable method for separating the optical antipode from the discriminating liquid is distillation and/or evaporation. In this case, the discriminating liquid must be continuously recovered and recycled, and it is very effective to combine a process which allows easy continuous separation such as distillation and/or evaporation.

Since the optical antipodes and the discriminating agent are likely to be deteriorated or racemized by heat, it is preferable to separate the antipode at a low temperature, and distillation under reduced pressure and/or evaporation under reduced pressure is especially preferable.

Furthermore, it is preferable to racemize one of the optically resolved optical isomers for recycling.

The technique of the present invention can be used in the following style in a process of distillation separation such as extractive distillation separation or absorption separation. It is preferable to carry out distillation separation or absorption separation under conditions that avoid precipitation of any crystals in the process. The crystals precipitated in the process of the present invention include the following three major types.

Crystals of a first type are formed when the discriminating agent, optical isomers and diluent are partially precipitated in a tower due to a change in the concentration of the diluent in the process system.

Crystals of a second type are formed when the discriminating agent, optical isomers and diluent are partially precipitated due to the change in the temperature of the process system.

Crystals of a third type are formed when a diastereomeric salt or inclusion compound (clathrate compound) is produced by mixing of the discriminating liquid and the optical isomers to be resolved, or formed in relation with solubility. The production of a diastereomeric salt or inclusion compound certainly dramatically raises the optical purity of the precipitated optical antipode, but it is disadvantageous from the view point of handling in a process such as solid-liquid separation.

In the present invention, the separation under conditions to avoid precipitation of crystals provides an advantage that the complication in a continuous process such as countercurrent contact can be prevented. That is, since the solution can be treated as a homogeneous solution, the optical antipodes can be enhanced in purity in continuous production in a multi-step process, and smooth production can be ensured.

As the conditions avoid precipitation of crystals in the present invention, the following conditions must be satisfied.

(1) The discriminating agent, optical isomers and diluent are not precipitated in the process system, even if they change in concentration within the respective service concentration ranges.

(2) The discriminating agent, optical isomers and diluent are not precipitated in the process system, even if the temperature changes within the service temperature range.

(3) The discriminating agent and the optical isomers to be dissolved are of the concentrations not causing any precipitation even if a diastereomeric salt or inclusion compound is formed by the reaction between them in the process system, or the discriminating agent and the optical isomers to be resolved are of a combination not causing precipitation at all.

The condition (3) can be verified by sampling at respective portions in the tower for concentration analysis.

The discriminating liquid in distillation separation or absorption separation in the present invention possesses the following properties when the optical isomers to be resolved and the discriminating liquid are mixed to prepare a solution under the conditions that prevent precipitation of crystals for measuring the gas-liquid equilibrium composition, the ratio between the optical isomers in the gaseous phase is different from the ratio between the optical isomers mixed at first. The discriminating liquid has an effect of acting to keep the relative volatility between the optical isomers in the gaseous phase and the optical isomers in the liquid phase at other than 1. In this case, the ratio between the optical isomers in the gaseous phase or the ratio between the optical isomers in the liquid phase means, for example, the ratio between an R isomer and an S isomer. The isomer ratio can be simply measured by generally known liquid chromatography or gas chromatography for analysis of optical isomers.

It is preferable that the ratio by weight of the discriminating agent to the diluent in the discriminating liquid is 1% or more. More preferable is 5% or more, and further more preferable is 10% or more. Still further more preferable is 30% or more, and an especially preferable range is 30 to 80%. Furthermore, in the present invention, it is preferable that the respective components of the discriminating liquid have a higher in boiling point than the optical isomers to be resolved, or are not volatilized. Moreover, it is preferable that the discriminating liquid sufficiently dissolves the mixture containing the optical isomers to be resolved.

Figure 2:
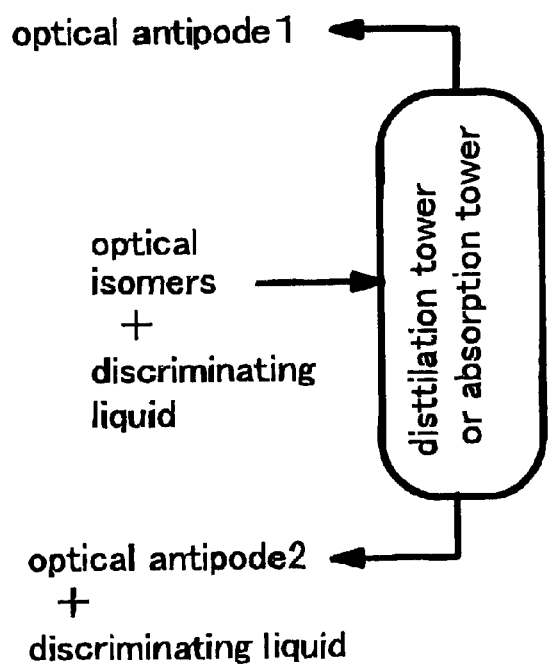
FIG. 2 shows the an absorption separator operation of the present invention.

The above method for resolving optical isomers basically uses distillation separation or absorption separation. All the merits of the so-called extractive distillation process and the absorption separation process known hitherto can be used in the method of the present invention. In the present invention, it is preferable to bring the discriminating liquid and the optical isomers to be resolved into contact with each other in respectively reverse directions, as so-called countercurrent contact. In the distillation separation or absorption separation process, it is especially preferable to continuously inject the discriminating liquid into an upper stage of a distillation tower or absorption tower and to continuously inject the mixture containing the optical isomers to be resolved, into a middle stage of the distillation tower or absorption tower. Preferable apparatuses are shown in FIGS. 1 and 2, and it is preferable to continuously resolve.

That is, in the present invention, it is preferable to use a separator in which the discriminating liquid is continuously injected into an upper stage of a distillation tower or absorption tower while the mixture containing the optical isomers to be resolved is continuously injected into a middle stage of the distillation tower and the absorption tower. Furthermore, even a separator in which the mixture containing the optical isomers to be resolved and the discriminating liquid are continuously injected into a middle stage of a distillation tower or absorption tower can also be preferably used for resolution. Moreover, a separator in which the discriminating liquid is continuously injected into an upper stage of a distillation tower or absorption tower while the mixture containing the optical isomers to be resolved and the discriminating liquid are continuously injected into a middle stage of the distillation tower or absorption tower can also be preferably used.

As a more preferable resolution method in the present invention, the solution containing the discriminating liquid and an optical antipode is taken out of a lower stage of a distillation tower or absorption tower, and the discriminating liquid is separated from the optical antidope and returned to the distillation tower or absorption tower, since the separation method is efficient and economical. p Furthermore, it is a more preferable separation method that the unknown optical antipode component in the optical antipode component taken out of an upper stage or lower stage of the distillation tower or absorption tower is racemized and returned to the process as optical isomers to be separated.

It is preferable that the distillation separation or absorption separation of optical isomers is carried out at a temperature as low as possible, since the discriminating agent and the resolved optical antipode are likely to be isomerized or structurally changed by heat. For carrying out the separation at a temperature as low as possible, it is preferable to reduce the pressure in the process system for resolution. It is preferable that the tower bottom temperature of the distillation tower is kept in a range from 40 to 300° C. A more preferable range is 40 to 200° C. It is especially preferable that the tower bottom temperature of the distillation tower is kept in a range from 40 to 200° C. and that distillation separation or absorption separation is carried out under reduced pressure.

The technique of the present invention can be used in the following style in the adsorption separation process.

In the adsorption separation process of the present invention, since the discriminating liquid comprising the discriminating agent and the diluent functions as a mobile phase, it must have a capability to desorb the optical isomers adsorbed by an adsorbent.

In the adsorption separation process, for letting the discriminating liquid manifest a sufficient desorbability for efficient processing, it is preferable that the adsorption selection coefficient $\alpha_{A/B}$ between one optical antipode A in the mixture containing optical isomers and the diluent B is 0.1 to 10.0. A more preferable range is 0.2 to 5.0.

In the present invention, the property of the adsorbent is expressed by the adsorption selection coefficient $\alpha_{A/B}$ of the following formula:

$\alpha_{A/B}$=([Adsorbing phase A]/[Adsorbing phase B])/ ([Liquid phase A]/[Liquid phase B]).

The adsorption selection coefficient can be calculated by analyzing the concentrations of respective components of the liquid phase, [absorbing phase A], [adsorbing phase B], [liquid phase A] and [liquid phase B] by liquid chromatography or gas chromatography. It is preferable to decide the concentrations of respective components by the internal standard method. A preferable internal standard is n-nonane, but if n-nonane cannot be dissolved since the mobile phase is soluble in water or is a polar solvent, etc., any appropriate non-adsorbable component must be selected as the internal standard.

When $\alpha_{A/B}$ is larger than 1, component A is adsorbed and when smaller than 1, component B is adsorbed. If this value is too large, the adsorption separation efficiency is lowered since the optical isomers adsorbed by the adsorbent are unlikely to be desorbed by the diluent, and if the value is too small, the adsorption separation efficiency is lowered since the optical antipode is unlikely to be adsorbed by the adsorbent.

In the present invention, a specific optical antipode is obtained from the mixture containing optical isomers using an optically active discriminating agent, diluent and adsorbent. The discriminating liquid, i.e., the discriminating agent in the mobile phase discriminates a specific optical antipode in the mixture containing optical isomers by complex formation, hydrogen bond or molecular interaction such as p-p interaction. A specific optical antipode not amenable to be discriminated is likely to be adsorbed by an adsorbent, and a specific optical antipode amenable to be discriminated is unlikely to be adsorbed by an adsorbent. This principle can be used for adsorption separation of optical isomers.

As adsorption separation using the method of the present invention, adsorption separation by using a moving bed or simulated moving bed is preferable. Especially continuous adsorption separation by using a simulated moving bed is preferable as an industrial process and can sufficiently use the merits of the present invention.

As the basic operations of adsorption separation by using a simulated moving bed, the following adsorbing operation, concentrating operation and desorbing operation are continuously repeated.

(1) Adsorbing operation: A mixture containing optical isomers is brought into contact with an adsorbent, and a strongly adsorbable component is adsorbed selectively leaving a weakly adsorbable component. The strongly adsorbable component is recovered as an extract component together with the mobile phase containing an optically active discriminating agent.

(2) Concentrating operation: The raffinate containing a large amount of the weakly adsorbable component is further brought into contact with the adsorbent, to selectively adsorb the strongly adsorbable component, causing the weakly adsorbable component in the raffinate to be highly purified.

(3) Desorbing operation: The highly purified weakly adsorbable component is recovered as the raffinate, and on the other hand, the strongly adsorbable component is expelled from the adsorbent by the discriminating liquid containing an optically active compound, being recovered as the extract component together with the discriminating liquid.

In this method, the component obtained from the extract can also be highly purified. Furthermore, the optical antipode not intended can also be recovered and isomerized, to be returned into the process.

In the adsorption separation process of the present invention, when an optical antipode is separated from the discriminating liquid, to be obtained as a highly pure optical antipode product while the mobile phase component is recovered and returned, or when the unwanted isomer is separated while the discriminating liquid components are recovered and returned, the conditions of the present invention are important, that (c) the boiling point of at least one compound of the discriminating agent at the pressure of resolving operation is higher than the boiling point of at least one compound of the diluent at the pressure of the resolving operation, and/or that (d) the boiling point of at least one compound of the diluent at the pressure of the resolving operation is higher than the boiling point of the optical isomers to be resolved, at the pressure of the resolving operation by 10° C. or more.

The effect of the present invention is described below in reference to examples.

1. PREPARATION OF DISCRIMINATING LIQUIDS

<Preparation of heptakis(2,6-O-dipentyl)-β-cyclodextrin>

Heptakis(2,6-O-dipentyl)-β-cyclodextrin (DP-B-CD) was prepared as described below in reference to G. Wenz, Carbohydrate Research, 214, 257–265p. (1991).

2144.6 grams of β-cyclodextrin (produced by Nippon Shokuhin Kako) was dissolved into 10.18 liters of DMSO (produced by Toray Fine Chemical). To the solution, 4794.4 g of 1-bromopentane (produced by Toso) was added, and to the mixture, 1322.0 g of granular NaOH (produced by Katayama Kagaku Kogyo) was added gradually. The mixture was stirred at room temperature for about 4 days, and an excessive mount of n-hexane was added to it. The mixture was stirred, and the supernatant solution phase was extracted. This operation was repeated 3 times. The organic phase was washed by saturated saline solution 3 times, and sodium sulfate was added for drying. Then, n-hexane was removed at room temperature and a reduced pressure of about 1 mm Hg. Furthermore, the residue was gradually heated to 100° C., to distill away low boiling point compounds, for obtaining DP-B-CD.

<Preparation of heptakis(2,6-O-dipentyl-3-O-trifluoroacetyl)-β-cyclodextrin (DPTFA-B-CD)>

Heptakis(2,6-O-dipentyl-3-O-trifluoroacetyl)-β-cyclodextrin (DPTFA-B-CD) was prepared as described below in reference to W. Y. Li, H. L. Jin, D. W. Armstrong, J. Chromatogr., 509, 303–324p, (1990).

1000 grams of heptakis(2,6-O-dipentyl)-β-cyclodextrin was dissolved into 5000 g of n-hexane. With stirring, to the solution, 4000 g of trifluoroacetic anhydride (produced by Asahi Glass) was gradually added dropwise. The mixture was stirred overnight, washed with water 3 times, and neutralized by saturated sodium hydrogencarbonate aqueous solution. The mixture was further washed with water.

Furthermore, it was concentrated by an evaporator, to remove n-hexane, for obtaining DPTFA-B-CD as an discriminating agent.

<Preparation of heptakis(2,6-O-dihexyl)-β-cyclodextrin>

Heptakis(2,6-O-dihexyl)-β-cyclodextrin (DHx-B-CD) was prepared as described below in reference to G. Wenz, Carbohydrate Research, 214, 257–265p (1991).

25.0 grams of β-cyclodextrin (produced by Nippon Shokuhin Kako) was dissolved into 150 ml of DMSO (produced by Toray Fine Chemical). To the solution, 15.1 g of 0.7 mm granular NaOH (produced by Kishida Kagaku) was added, and the mixture was stirred. To it, 61.1 g of 1-bromohexane (produced by Tokyo Kasei) was added taking 1 hour, and the mixture was heated to 70° C. and stirred for about 8 hours. To it, 100 ml of n-hexane was added, and 20% saline solution was added. The organic phase was extracted, and to it, 100 ml of 20% saline solution was added. The mixture was stirred, and the organic phase was extracted. The organic phase was washed with 100 ml of 20% saline solution, and to it, 20 ml of n-paraffin SL (produced by Nippon Sekiyu Kagaku) was added. At 60° C. and a reduced pressure of 50 mm Hg, n-hexane was removed, and at 120° C. and a reduced pressure of 20 mm Hg, n-paraffin and unreactive 1-bromohexane and 1-hexanol were distilled away, to obtain DHx-B-CD.

<Preparation of heptakis(2,6-O-dihexyl-3-O-trifluoroacetyl)-β-cyclodextrin (DHxTFA-B-CD)>

Heptakis(2,6-O-dihexyl-3-O-trifluoroacetyl)-β-cyclodextrin (DHxTFA-B-CD) was prepared as described below in reference to W. Y. Li, H. L. Jin, D. W. Armstrong, J. Chromatogr., 509, 303–324p (1990).

43.3 grams of heptakis(2,6-O-dihexyl)-β-cyclodextrin was dissolved into 65 ml of diisopropyl ether (produced by Nippon Sekiyu Kagaku). With stirring, to the solution, 35.7 g of trifluoroacetic anhydride (produced by Asahi Glass) was gradually added dropwise. The mixture was stirred at 25° C. for 12 hours, and the solvent was distilled away at 50° C. and a reduced pressure of 60 mm Hg. To the residue, 150 ml of diisopropyl ether was added for dissolution, and 10% sodium carbonate aqueous solution was added for neutralization. Furthermore, the organic phase was washed with 100 ml of 20% saline solution, and again washed with 100 ml of 20% saline solution. To the organic phase, 50 ml of n-paraffin SL was added, and at 60° C. and a reduced pressure of 50 mm Hg, diisopropyl ether was removed. Then, at 120° C. and a reduced pressure of 20 mm Hg, n-paraffin was distilled away, to obtain 48.0 g of DhxTFA-B-CD.

<Preparation of heptakis(2,6-O-dioctyl)-β-cyclodextrin>

100.0 grams of β-cyclodextrin (produced by Nippon Shokuhin Kako) was dissolved into 600 ml of DMSO (produced by Toray Fine Chemical). To the solution, 75.0 g of 0.7 mm granular NaOH (produced by Kishida Kagaku) was added, and the mixture was stirred. To it, 286.0 g of 1-bromooctane (produced by Tokyo Kasei) was added taking 1 hour, and the mixture was heated to 70° C. and stirred for about 8 hours. To the mixture, 500 ml of n-hexane was added, and the mixture was stirred. To it, 20% saline solution was added, and the organic phase was extracted. To the organic phase, 400 ml of 20% saline solution was added, and the mixture was stirred. The organic phase was extracted and washed with 500 ml of 20%. saline solution, and to the organic phase, 100 ml of n-paraffin SL (produced by Nippon Sekiyu Kagaku) was added. At 60° C. and a reduced pressure of 50 mm Hg, n-hexane was removed, and at 120° C. and a reduced pressure of 20 mm Hg, n-paraffin and unreactive 1-bromooctane and 1-octanol were distilled away, to obtain DO-B-CD. It was developed on Silica Gel 60F254 TLC Plate (produced by Merck) using a developing solvent (hexane:ethyl acetate=3:3 by volume), and Rf was found to be 0.65.

<Preparation of heptakis(2,6-O-dioctyl-3-O-trifluoroacetyl)-β-cyclodextrin (DOTFA-B-CD)>

238 grams of heptakis(2,6-O-dioctyl)-β-cyclodextrin was dissolved into 400 ml of diisopropyl ether (produced by Nippon Sekiyu Kagaku). With stirring, to the solution, 160 g of trifluoroacetic anhydride (produced by Asahi Glass) was gradually added dropwise, and the mixture was stirred at 25° C. for 12 hours. The solvent was distilled away at 50° C. and a reduced pressure of 60 mm Hg, and to the residue, 500 ml of diisopropyl ether was added for dissolution. To the mixture, 10% sodium carbonate aqueous solution was added for neutralization, and the organic phase was washed with 200 ml of 20% saline solution, and again washed with 200 ml of 20% saline solution. To the organic phase, 200 ml of n-paraffin SL was added, and at 60° C. and a reduced pressure of 50 mm Hg, diisopropyl ether was removed. Then at 120° C. and a reduced pressure of 20 mm Hg, n-paraffin was distilled away, to obtain 280.0 g of DO-TFA-B-CD. It was developed by Silica Gel 60F254 TLC Plate (produced by Merck) using a developing solvent (hexane:ethyl acetate=3:1 by volume), and Rf was found to be 0.83.

<Preparation of heptakis(2,6-O-dioctyl-3-O-acetyl)-β-cyclodextrin (DOAc-B-CD)>

7.1 grams of heptakis(2,6-O-dioctyl)-β-cyclodextrin and 2.2 g of 4-dimethylaminopyridine were dissolved into 40 ml of triethylamine (produced by Katayama Kagaku). With stirring, to the solution, 2.3 g of acetic anhydride (produced by Nakarai Tesk) was gradually added dropwise, and the mixture was stirred at 25° C. for 7 hours. The solvent was distilled away at 50° C. and a reduced pressure of 60 mm Hg, and to the residue, 50 ml of diisopropyl ether was added for dissolution. To the mixture, 10% hydrochloric acid was added for neutralization, and the organic phase was washed with 200 ml of water. To the organic phase, 20 ml of n-paraffin SL was added, and at 60° C. and a reduced pressure of 50 mm Hg, diisopropyl ether was removed. Furthermore at 120° C. and a reduced pressure of 20 mm Hg, n-paraffin was distilled away, to obtain 8.1 g of DOAc-B-CD. It was developed by Silica Gel 60F254 TLC Plate (produced by Merck) using a developing solution (hexane 5-butyl methyl ether=1:1 by volume), and Rf was found to be 0.52.

<Preparation of heptakis(2,6-O-dioctyl-3-O-propionyl)-β-cyclodextrin (DOPR-B-CD)>

7.0 grams of heptakis(2,6-O-dioctyl)-β-cyclodextrin and 1.1 g of 4-dimethylaminopyridine were dissolved into 40 ml of triethylamine (Katayama Kagaku). With stirring, to the solution, 2.9 g of propionic anhydride (produced by Nakarai Tesk) was gradually added dropwise, and the mixture was stirred at 25° C. for 6 hours. The solvent was distilled away at 50° C. and a reduced pressure of 60 mm Hg, and to the residue, 50 ml of diisopropyl ether was added for dissolution. To the mixture, 10% hydrochloric acid was added for neutralization, and the organic phase was washed with 200 ml of water. To the organic phase, 20 ml of n-paraffin SL was added, and at 60° C. and a reduced pressure of 50 mm Hg, diisopropyl ether was removed. Furthermore at 120° C. and a reduced pressure of 20 mm Hg, n-paraffin was distilled away, to obtain 8.5 g of DOPr-B-CD. It was developed by Silica Gel 60F254 TLC Plate (produced by Merck) using a developing solvent (hexane t-butyl methyl ether=1:1 by volume), and Rf was found to be 0.56.

<Preparation of heptakis(2,6-O-dioctyl-3-O-butyryl)-β-cyclodextrin (DOBu-B-CD)>

8.7 grams of heptakis(2,6-O-dioctyl)-β-cyclodextrin and 1.4 g of 4-dimethylaminopyridine were dissolved into 40 ml of triethylamine (produced by Katayama Kagaku). With stirring, to the solution, 4.3 g of butyric anhydride (produced by Tokyo Kasei) was gradually added dropwise, and the mixture was stirred at 25° C. for 6 hours. The solvent was distilled away at 50° C. and a reduced pressure of 60 mm Hg, and to the residue, 50 ml of diisopropyl ether was added for dissolution. To the mixture, 10% hydrochloric acid was added for neutralization, and the organic phase was washed with 200 ml of water. To the organic phase, 20 ml of n-paraffin SL was added, and at 60° C. and a reduced pressure of 50 mm Hg, diisopropyl ether was removed. Furthermore at 120° C. and a reduced pressure of 20 mm Hg, n-paraffin was distilled away to obtain 9.6 g of DOBu-B-CD. It was developed by Silica Gel 60F254 TLC Plate (produced by Merck) using a developing solvent (hexane:t-butyl methyl ether=1:1 by volume), and Rf was found to be 0.57.

<Preparation of heptakis(2,6-O-dioctyl-3-O-valeryl)-β-cyclodextrin (DOVa-B-CD)>

9.0 grams of heptakis(2,6-O-dioctyl)-β-cyclodextrin and 1.4 g of 4-dimethylaminopyridine were dissolved into 40 ml of triethylamine (produced by Katayama Kagaku). With stirring, to the solution, 5.2 g of valeric anhydride (produced by Tokyo Kasei) was gradually added dropwise, and the mixture was stirred at 25° C. for 6 hours. The solvent was distilled away at 50° C. and a reduced pressure of 60 mm Hg, and to the residue, 50 ml of diisopropyl ether was added for dissolution. To the mixture, 10% hydrochloric acid was added for neutralization, and the organic layer was washed with 200 ml of water. To the organic phase, 20 ml of n-paraffin SL was added, and at 60° C. and a reduced pressure of 50 mm Hg, diIsopropyl ether was removed. Furthermore at 120° C. and a reduced pressure of 20 mm Hg, n-paraffin was distilled away to obtain 11.3 g of DOVa-B-CD. It was developed by Silica Gel 60F254 TLC Plate (produced by Merck) using a developing solvent (hexane t-butyl methyl ether=1:1 by volume), and Rf was found to be 0.60.

<Preparation of heptakis(2,6-O-dioctyl-3-O-hexanoyl)-β-cyclodextrin (DOHx-B-CD)>

5.5 grams of heptakis(2,6-O-dioctyl)-β-cyclodextrin and 0.8 g of 4-dimethylaminopyridine were dissolved into 20 ml of triethylamine (produced by Katayama Kagaku). With stirring, to the solution, 3.7 g of hexanoic anhydride (produced by Tokyo Kasei) was gradually added dropwise. The mixture was stirred at 25° C. for 6 hours, and the solvent was distilled away at 50° C. and a reduced pressure of 60 mm Hg. To the residue, 50 ml of diisopropylether was added for dissolution, and 10% hydrochloric acid was added for neutralization. The organic phase was washed with 200 ml of water, and to the organic phase, 20 ml of n-paraffin SL was added. At 600 C and a reduced pressure of 50 mm Hg, diisopropyl ether was removed, and at 120° C. and a reduced pressure of 20 mm Hg, n-paraffin was distilled away to obtain 11.3 g of DOHx-B-CD. It was developed by Silica Gel 60F254 TLC Plate (produced by Merck) using a developing solvent (hexane:t-butyl methyl ether=1:1 by volume), and Rf was found to be 0.64.

<Preparation of heptakis(2,6-O-didecyl)-β-cyclodextrin>

6.1 grams of β-cyclodextrin (produced by Nippon Shokuhin Kako) was dissolved into 50 ml of DMSO (produced by Toray Fine Chemical). To the solution, 4.0 g of powdery NaOH (produced by Katayama Kagaku Kogyo) was added, and the mixture was stirred. To the mixture, 20.0 g of 1-bromodecane (produced by Tokyo Kasei) was added taking 5 minutes, and the mixture was heated to 70° C. and stirred for about 12 hours. To the mixture, 100 ml of n-hexane was added, and the mixture was stirred. To the mixture, 20% saline solution was added, and the organic phase was extracted. To the organic phase, 100 ml of 20% saline solution was added, and the mixture was stirred. The organic phase was extracted and washed with 100 ml of 20% saline solution, and to the organic phase, 20 ml of n-paraffin SL (produced by Nippon Sekiyu Kagaku) was added. At 60° C. and a reduced pressure of 50 mm Hg, n-hexane was removed and at 120° C. and a reduced pressure of 20 mm Hg, n-paraffin and unreactive 1-bromodecane and 1-decanol were distilled away, to obtain DD-B-CD. It was developed by Silica Gel 60F254 TLC Plate (produced by Merck) using a developing solvent (hexane:ethyl acetate=3:1 by volume), and Rf was found to be 0.68.

<Preparation of heptakis(2,6-O-didecyl-3-O-trifluoroacetyl)-β-cyclodextrin (DDTFA-B-CD)>

15.0 grams of heptakis(2,6-O-didecyl)-β-cyclodextrin was dissolved into 50 ml of diisopropyl ether (produced by Nippon Sekiyu Kagaku). With stirring, to the solution, 14 g of trifluoroacetic anhydride (produced by Asahi Glass) was gradually added dropwise, and the mixture was stirred at 25° C. for 20 hours. The solvent was distilled away at 50° C. and a reduced pressure of 60 mm Hg, and to the residue, 50 ml of diisopropyl ether was added for dissolution. To the mixture, 10% sodium carbonate aqueous solution was added for neutralization, and the organic phase was washed with 50 ml of 20% saline solution, and again washed with 50 ml of 20% saline solution. To the organic phase, 20 ml of n-paraffin SL was added, and at 60° C. and a reduced pressure of 50 mm Hg, diisopropyl ether was removed. Furthermore at 120° C. and a reduced pressure of 20 mm Hg, n-paraffin was distilled away, to obtain 15.9 g of DDTFA-B-CD. It was developed by Silica Gel 60F254 TLC Plate (produced by Merck) using a developing solvent (hexane:ethyl acetate=3:1 by volume), and Rf was found to be 0.84.

<Preparation of heptakis(2,6-O-butyl)-β-cyclodextrin>

6.1 grams of β-cyclodextrin (produced by Nippon Shokuhin Kako) was dissolved into 50 ml of DMSO (produced by Toray Fine Chemical). To the solution, 4.0 g of powdery NaOH (produced by Katayama Kagaku Kogyo) was added and the mixture was stirred. To the mixture, 12.4 g of 1-bromodecane (produced by Tokyo Kasei) was added taking 5 minutes, and the mixture was heated to 70° C. and stirred for about 12 hours. To the mixture, 100 ml of n-hexane was added, and the mixture was stirred. Then 20% saline solution was added, and the organic phase was extracted. To the organic phase, 100 ml of 20% saline solution was added, and the mixture was stirred. The organic layer was extracted and washed with 100 ml of 20% saline solution, and to the organic layer, 20 ml of n-paraffin SL (produced by Nippon Sekiyu Kagaku) was added. At 60° C. and a reduced pressure of 50 mm Hg, n-hexane was removed and at 120° C. and a reduced pressure of 20 mm Hg, n-paraffin and unreactive 1-bromobutane and 1-butanol were distilled away to obtain DBu-B-CD.

<Preparation of heptakis(2,6-O-dibutyl-3-O-propionyl)-β-cyclodextrin (DBuPr-B-CD)>

7.3 grams of heptakis(2,6-O-dibutyl)-β-cyclodextrin and 1.6 g of 4-dimethylaminopyridine were dissolved into 40 ml of triethylamine (produced by Katayama Kagaku). With stirring, to the solution, 4.1 g of propionic anhydride (produced by Nakarai Tesk) was gradually added dropwise. The mixture was stirred at 25° C. for 8 hours, and the solvent was distilled away at 50° C. and a reduced pressure of 60 mm Hg. To the residue, 50 ml of diisopropyl ether was added for dissolution, and 10% hydrochloric acid was added for neutralization. The organic phase was washed with 200 ml of water, and to the organic phase, 20 ml of n-paraffin SL was added. At 60° C. and a reduced pressure of 50 mm Hg, diisopropyl ether was removed, and at 120° C. and a reduced pressure of 20 mm Hg, n-paraffin was distilled away to obtain 8.3 g of DBuPr-B-CD. It was developed by Silica Gel 60F254 TLC Plate (produced by Merck) using a developing solvent (hexane ethyl acetate=3:1 by volume), and Rf was found to be 0.52.

<Preparation of heptakis(2,6-O-butyl-3-O-trifluoroacetyl)-β-cyclodextrin (DBuTFA-B-CD)>

12.0 grams of heptakis(2,6-O-dibutyl)-β-cyclodextrin was dissolved into 50 ml of diisopropyl ether (produced by Nippon Sekiyu Kagaku). With stirring, to the solution, 12 g of trifluoroacetic anhydride (produced by Asahi Glass) was gradually added dropwise, and the mixture was stirred at 25° C. for 20 hours. The solvent was distilled away at 50° C. and a reduced pressure of 60 mm Hg, and to the residue, 50 ml of diisopropyl ether was added for dissolution. To the mixture, 10% sodium carbonate aqueous solution was added for neutralization, and the organic phase was washed with 50 ml of 20% saline solution, and again washed with 50 ml of 20% saline solution. To the organic phase, 20 ml of n-paraffin SL was added, and at 60° C. and a reduced pressure of 50 mm Hg, diisopropyl ether was removed. Furthermore at 120° C. and a reduced pressure of 20 mm Hg, n-paraffin was distilled away to obtain 14.5 g of DBuTFA-B-CD. It was developed by Silica Gel 60F254 TLC Plate (produced by Merck) using a developing solvent (hexane:ethyl acetate=3:1 by volume), and Rf was found to be 0.79.

2. RESOLUTION OF OPTICAL ISOMERS BY DISTILLATION SEPARATION

EXAMPLE 1

An Oldershaw type 40-plate distillation tower with an inner diameter of 40 mm was used for an experiment. From an upper part of a condenser at the top of the distillation tower, an discriminating liquid and a mixture of optical isomers to be resolved (a solution consisting of DPTFA-B-CD:n-nonane (produced by Tokyo Kasei):methyl RS-2-chloropropionate (produced by Tokyo Kasei)=62:33:5 (by weight), optical purity of methyl RS-2-chloropropionate 50%) kept at a reduced pressure of 15 mm Hg by a vacuum pump at the tower top and kept at 50° C. were continuously introduced into the tower at about 20 g/min. The tower bottom temperature was kept at 85° C., and the bottom solution was taken out at about 14.5 g/min continuously from the tower bottom, while a distillate was continuously taken out from the tower top at a reflux ratio of 0.20.

After operation for several hours for stabilization, the tower bottom solution and the distillate were obtained in containers, and their components were analyzed respectively. The optical purity of methyl R-2-chloropropionate in the distillate was 54%, and the optical purity of methyl S-2-chloropropionate in the tower bottom solution was 87%. The R and S isomers were analyzed by gas chromatography using Chiraldex. B-TA Capillary Column (produced by ASTEC). From the tower bottom solution, n-nonane and methyl 2-chloropropionate were separated and recovered by an evaporator, and n-nonane was added to re-prepare an discriminating liquid composed as stated above (DPTFA-B-CD:n-nonane (produced by Tokyo Kasei)=62:33 (by weight)) for recycled use. The re-prepared discriminating liquid was analyzed and found to contain less than 1 wt % of optical isomers, methyl RS-2-chloropropionate. Even when the re-prepared discriminating liquid was used, similar experimental results of distillation could be obtained. The evaporation residue of the tower bottom solution by, the evaporator and the distillate were separated in the distillation tower, and the obtained n-nonane was recycled. It was confirmed that by recycling the discriminating liquid satisfying the conditions of the present invention, the process of the present invention could be carried out continuously.

The above example could show that if the conditions of the present invention are satisfied, optical isomers can be efficiently resolved.

EXAMPLE 2

An Oldershaw type 20-plate distillation tower with an inner diameter of 40 mm was used for an experiment. From an upper part of a condenser at the top of the distillation tower, an discriminating liquid (a solution consisting of DPTFA-B-CD:n-paraffin SL (produced by Nippon Sekiyu Kagaku)=2:1 (by weight)) was continuously introduced into the tower at about 10.5 g/min. Beforehand at the tower bottom, 250 g of methyl RS-2-chloropropionate was introduced, and the tower bottom temperature was kept at 67° C. From the tower top, a distillate was taken out continuously at about 0.36 g/min.

After operation for 1 hour, the distillate was obtained in a container. Its components were analyzed, and the optical purity of methyl R-2-chloropropionate in the distillate was found to be 72%.

From the tower bottom solution, the discriminating liquid consisting of the discriminating agent (DPTFA-B-CD) and the diluent (n-paraffin SL) and the optical isomers (methyl RS-2-chloropropionate) were separated by an evaporator. The separation by the evaporator was carried out at a bath temperature of 95° C. and 5 mm Hg, to obtain a mixture consisting of the diluent and the optical isomers and another mixture consisting of the diluent and the discriminating agent. Then, a packed distillation tower was used to separate the optical isomers from the diluent. Since the boiling point difference between the discriminating agent and the diluent and the boiling point difference between the diluent and the optical isomers were respectively more than 10° C., separation could be easily achieved using the evaporator and the distillation tower.

The separated diluent and the mixture consisting of the diluent and the discriminating agent were mixed, and the same diluent was newly added to re-prepare an discriminating liquid composed as stated above (DPTFA-B-CD:n-paraffin SL=2:1 (by weight)). The re-prepared discriminating liquid was analyzed by gas chromatography, to confirm that the concentration of optical isomers, methyl RS-2-chloropropionate was lower than 1 wt %. The re-prepared discriminating liquid was recycled.

It was confirmed that by recycled use of an discriminating liquid satisfying the conditions of the present invention, the process of the present invention could be carried out continuously.

The properties of the discriminating liquid, etc. in this example are shown below.

Viscosity of the discriminating liquid: 0.09 Pa·s (80° C.)
  Dielectric constant of diluent (n-paraffin SL): 1.99~2.02 Boiling point of the discriminating agent: 150° C. or higher/30 mm Hg Boiling point of the diluent: 80~90° C./30 mm Hg Boiling point of the optical isomers to be separated: About 50° C./30 mm Hg Concentration of the discriminating agent: 66.7 wt %

By using n-paraffin SL with a low viscosity and a low dielectric constant as the diluent, an effect of lowering the viscosity of the discriminating liquid could be obtained with the discriminatability kept. The discriminating agent, DPTFA-B-CD itself has a very high viscosity and cannot be easily circulated or recycled in process, but in this example, it could be smoothly used without any problem.

(Measurement of $_1$H -NMR spectrum)

The $^1$H -NMR spectrum was measured under the following analysis conditions:

Instrument: Model UNITY INOVA Model 600 (produced by Varian)

Observation frequency: 599.8 MHz

Solvent: $CDCl_3$

Reference material: TMS

Number of points: 64 K

Observation width: 8 KHz

Pulse width: 45 degrees

Cycling time: 7 sec.

Integration times: 32

Figure 3:
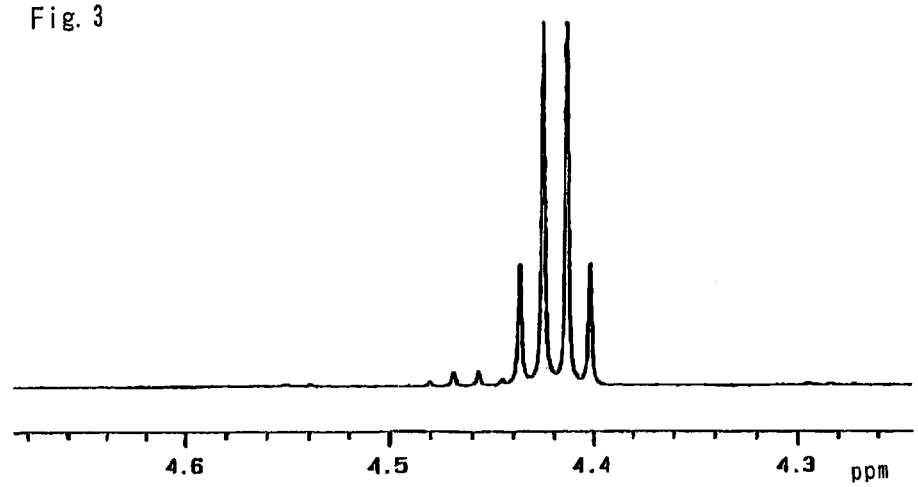
FIG. 3 shows an $^1$H-NMR spectrum of sample 1 (methyl RS-2-chloropropionate only, solvent $CDCl_3$) in Example 2.
Figure 4:
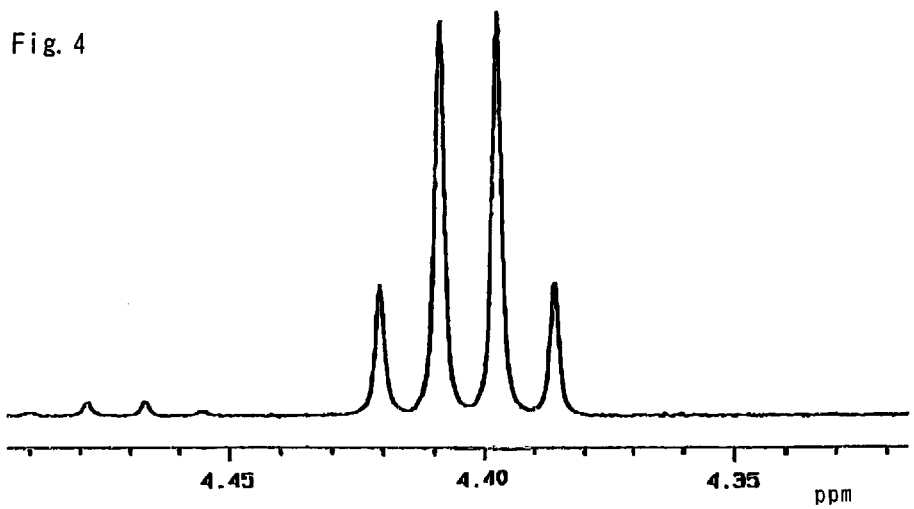
FIG. 4 shows an $^1$H-NMR spectrum of sample 2 (methyl S-2-chloropropionate+DPTFA-B-CD, solvent $CDCl_3$) in Example 2.
Figure 5:
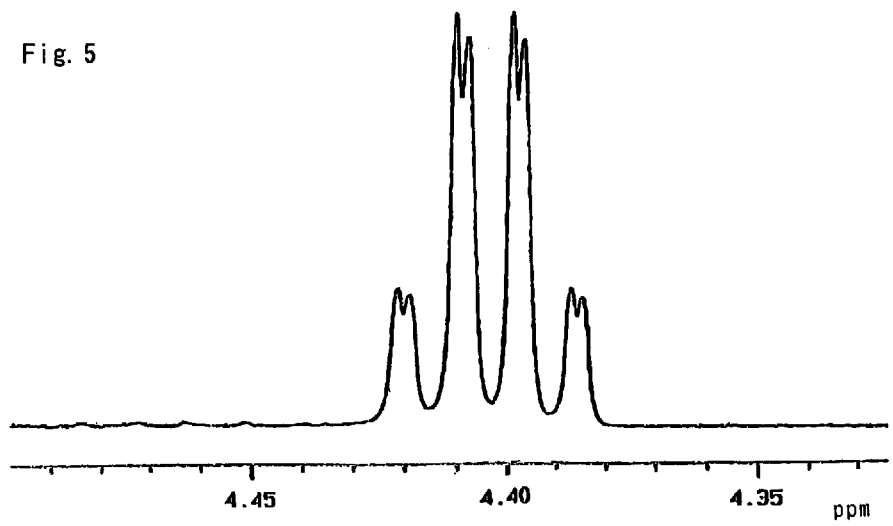
FIG. 5 shows an $^1$H-NMR spectrum of sample 3 (methyl RS-2-chloropropionate+DPTFA-B-CD, solvent $CDCl_3$) in Example 2.

Sample 1 with 20 mg of methyl RS-2-chloropropionate added to 900 mg of $CDCl_3$, sample 2 with 20 mg of methyl S-2-chloropropionate added to 900 mg of $CDCl_3$ and sample 3 with 20 mg of methyl RS-2-chloropropionate added to 900 mg of a solution of DPTFA-B-CD:$CDCl_3$ =1:1 (by weight) were measured under the above measuring conditions. The peaks (quadruple lines) of a-positions of methyl 2-chloropropionate in respective samples are shown in FIG. 3 (sample 1), FIG. 4 (sample 2) and FIG. 5 (sample 3).

With samples 1 and 2 of methyl 2-chloropropionate alone, a quadruple line could be obtained, but with sample 3 with DPTFA-B-CD added, splitting of a quadruple line was observed.

From the above result, it was confirmed that DPTFA-B-CD discriminates R and S isomers in methyl RS-2-chloropropionate.

The dielectric constant of $CDCl_3$ is 4.81. The dielectric constant of n-paraffin SL is in a range from 1.99 to 2.02, being smaller than that of $CDCl_3$.

(Measurement of relative volatility)

A solution consisting of DPTFA-B-CD n-paraffin SL (produced by Nippon Sekiyu):methyl RS-2- chloropropionate (produced by Tokyo Kasei)=2:1:0.2 (by weight) was prepared. The boiling point of n-paraffin SL is in a range from 182 to 212° C. The gas-liquid equilibrium of methyl RS-2-chloropropionate of this solution was measured according to a conventional method. The liquid phase was heated to 80° C., and the pressure was reduced: to 30 mm Hg. The solution was allowed to stand in a stable state for several hours, and the R-isomer/S-isomer of methyl RS-2-chloropropionate in the gaseous phase and that in the liquid phase were measured, and the relative volatility $\alpha_{R/S}$ was calculated from the following formula. If the relative volatility is 1, the isomers cannot be separated by simple distillation. If the relative volatility is larger than 1, the isomers can be separated by distillation or absorption, and if the value is larger, the isomers can be more easily separated. $\alpha_{R/S=}$(R-isomer/S-isomer ratio in gaseous phase)/(R-isomer/S-isomer ratio in liquid phase).

The analysis of R-isomer and S-isomer was performed by gas chromatography using Chiraldex B-TA Capillary Column (produced by ASTEC). The relative volatility $\alpha_{R/S}$ was 1.33. From the gas, an R-isomer rich liquid could be obtained (boiling point 45° C.) and from the bottom liquid, an S-isomer rich liquid could be obtained. That is, it could be confirmed that by using an discriminating liquid consisting of DPTFA-B-CD as an discriminating agent and n-paraffin SL as a diluent, methyl RS-2-choropropionate as optical isomers could be resolved. Furthermore, even when an experiment was performed using said recycled discriminating liquid, the same results could be obtained.

The above example could show that if the conditions of the present invention are satisfied, optical isomers can be efficiently resolved.

EXAMPLE 3

A distillation tower in which two 25 mm inner dia. 800 mm high packed towers packed with SULZER type experiment use packing EX, and twenty 35 mm inner dia. Oldershaw type plates were vertically connected was used for an experiment. From an upper part of a condenser at the top of the distillation tower, an discriminating liquid and a mixture of optical isomers to be resolved (a solution consisting of DOTFA-B-CD:menthane (produced by Nippon Terpene) :methyl RS-2-chloropropionate (produced by Tokyo Kasei)=64:32:4 (by weight), optical purity of methyl RS-2-chloropropionate 50%) kept at a reduced pressure of 11mm Hg by a vacuum pump at the tower top and kept at 50° C. was continuously introduced into the tower at 5.9 g/min. The tower bottom temperature was kept at 85° C., and from the tower bottom, a solution was continuously taken out at 4.5 g/min, while a distillate was continuously taken out from the tower top at a reflux ratio of 0.56. After several hours of stabilization, the tower bottom solution and the distillate were obtained in containers. Their components were analyzed. The optical purity of methyl R-2-chloropropionate in the distillate was 63%, and the optical purity of methyl S-2-chloropropionate in the tower bottom solution was 96%. The R-isomer and the S-isomer were analyzed by gas chromatography using Chiraldex B-TA Capillary Column (produced by ASTEC). From the tower bottom solution, menthane and methyl 2-chloropropionate were recovered by an evaporator. Menthane was added to re-prepare an discriminating liquid composed as state above (DOTFA-B-CD:menthane (produced by Nippon Terpene)=64:32 (by weight)). As a result of analysis, it was confirmed that the concentration of optical isomers, methyl RS-2-chloropropionate was less than 1 wt %. The evaporation residue of the tower bottom solution by an evaporator and the distillate were respectively separated in the distillation tower, and the obtained methane was recycled. The same effect as in Examples 1 and 2 was confirmed.

EXAMPLE 4

Gas-liquid equilibrium contact was effected as described for Example 2, except that a solution consisting of DOTFA-B-CD:n-paraffin SL (produced by Nippon Sekiyu) methyl RS-2-chloropropionate (produced by Tokyo Kasei)=2:1:0.2 (by weight) was prepared.

The relative volatility $\alpha_{R/S}$ was 1.52. From the gas, an R-isomer rich liquid could be obtained (boiling point 45° C.), and from the bottom solution, an S-isomer rich liquid could be obtained. It could be confirmed that if an discriminating liquid consisting of DOTFA-B-CD as an discriminating agent and n-paraffin SL as a diluent is used, methyl RS-2-chloropropionate as optical isomers can be resolved.

Since the boiling point difference between the discriminating agent (DOTFA-B-CD) and the diluent (n-paraffin SL) and the boiling point difference between the diluent and the optical isomers (methyl RS-2-chloropropionate) are respectively more than 10° C., DOTFA-B-CD, n-paraffin SL and optical antipodes could be easily separated by using an evaporator and a distillation tower. Furthermore, the separated compounds could be re-used to obtain similar results. From the above, the same effect as obtained in Example 2 could be confirmed.

EXAMPLE 5

Gas-liquid equilibrium contact was effected as described for Example 2, except that a solution consisting of DOTFA-B-CD:n-paraffin SL (produced by Nippon Sekiyu):methyl RS-2-chloropropionate (produced by Tokyo Kasei)=6:3:0.2 (by weight) was prepared.

The relative volatility $\alpha_{R/S}$ was 1.94. From the gas, an R-isomer rich liquid could be obtained (boiling point 45° C.), and from the bottom solution, an S-isomer rich liquid could be obtained. It could be confirmed that if an discriminating liquid consisting of DOTFA-B-CD as an discriminating agent and n-paraffin SL as a diluent is used, methyl RS-2-chloropropionate as optical isomers can be resolved.

Since the boiling point difference between the discriminating agent (DOTFA-B-CD) and the diluent (n-paraffin SL) and the boiling point difference between the diluent and the optical isomers (methyl RS-2-chloropropionate) were more than 10° C. respectively, DOTFA-B-CD, n-paraffin SL and optical antipodes could be easily separated by using an evaporator and a distillation tower, and furthermore the separated compounds could be reused to obtain similar results. From the above, the same effect as obtained in Example 2 could be confirmed.

EXAMPLE 6

Gas-liquid equilibrium contact was effected as described for Example 2, except that a solution consisting of DPTFA-B-CD:n-paraffin SL (produced by Nippon Sekiyu):methyl RS-2-chloropropionate (produced by Tokyo Kasei)= 62.4:31.2:6.4 (by weight) was prepared and that the temperature of the liquid phase was 85° C.

The relative volatility $\alpha_{R/S}$ was 1.21. By distillation, an R-isomer rich liquid could be obtained, and from the bottom solution, an S-isomer rich liquid could be obtained. That is, it could be confirmed that by using an discriminating liquid consisting of DPTFA-B-CD as an discriminating agent and n-paraffin SL as a diluent, methyl RS-2-chloropropionate as optical isomers could be separated.

From the above, the same effect as obtained in Example 2 could be confirmed.

EXAMPLE 7

Gas-liquid equilibrium contact was effected as described for Example 2, except that a solution consisting of DPTFA-B-CD:n-paraffin SL (produced by Nippon Sekiyu):RS-epichlorohydrin (produced by Tokyo Kasei)=63.1:31.5:5.4 (by weight) was prepared, that the temperature of the liquid phase was 60° C., and that the pressure in the system was 15 mm Hg. The relative volatility $\alpha_{R/S}$ was 1.06. That is, it could be confirmed that by using an discriminating liquid consisting of DPTFA-B-CD as an discriminating agent and n-paraffin SL as a diluent, RS-epichlorohydrin as optical isomers can be separated.

From the above, the same effect as obtained in Example 2 could be confirmed.

EXAMPLE 8

The bottom solution used in Example 6 was further heated and the solution remaining after taking out the optical isomers was used for performing an experiment as in Example 6. The bottom solution did not precipitate any crystal, to allow the experiment to be continuously repeated. The DPTFA-B-CD/methyl 2-chloropropionate ratio in the solution was 14.37, and the R-isomer/S-isomer ratio of methyl 2-chloropropionate was 0.73. In this case, the relative volatility was 1.62. By a process increased in the number of steps, an S-isomer richer antipode liquid could be obtained. From the above, the same effect as obtained in Example 6 could be confirmed.

EXAMPLE 9

The bottom solution used in Example 8 was further heated, and the solution remaining after taking out the optical isomers was used to perform an experiment as in Example 6. The DPTFA-B-CD/methyl 2-chloropropionate ratio in the solution was 24.47, and the R-isomer/S-isomer ratio of methyl 2-chloropropionate was 0.53. In this case, the relative volatility was 1.83. According to a process increased in the number of steps, an S-isomer further richer optical antipode liquid could be obtained. From the above, the same effect as obtained in Example 6 could be confirmed.

Comparative Example 1

An experiment was performed as described for Example 1, except that the solution used was methyl RS-2-chloropropionate only. The relative volatility was 1.00. From this, it can be seen that the distillation separation of methyl RS-chloropropionate as optical isomers cannot be effected without using any discriminating liquid containing an optically active discriminating agent.

Comparative Example 2

An experiment was performed as described for Example 2, except that the solution used was RS-epichlorohydrin only. The relative volatility was 1.00. From this, it can be seen that distillation separation of RS-epichlorohydrin as optical isomers cannot be effected without using any discriminating liquid containing an optically active discriminating agent.

3. RESOLUTION OF OPTICAL ISOMERS BY ADSORPTION SEPARATION

EXAMPLE 10

(Evaluation of adsorption separability)

A solution consisting of DPTFA-B-CD diisopropyl ether-:methyl RS-2-chloropropionate (produced by A. H. Marks)= 46.59:46.77:6.63 (by weight) was prepared, and 3.00 g of it was supplied into an Erlenmeyer flask with a ground stopper. Into it, 1.0 g of silica gel 4B (produced by Fuji Silicia) dried at 200° C. for 10 hours was added. The mixture was allowed to stand at room temperature. for 1 hour, stirred sufficiently and allowed to stand for further 1 hour. Then, the supernatant solution was taken and its components were analyzed by gas chromatography using Chiraldex B-TA Capillary Column (produced by ASTEC). The calculated adsorption selection coefficient a R-isomer/S-isomer was 1.31, and a R-isomer/diisopropyl ether, 0.960. From the result, it can be seen that if DPTFA-B-CD is used as an optically active discriminating agent while silica gel is used as an adsorbent, the R-isomer and the S-isomer can be separated by adsorption. It can also be seen that since the adsorption selection coefficient R-isomer/diisopropyl ether is about 1, diisopropyl ether has sufficient desorbability and can be used as a diluent.

(Preparation of discriminating liquid)

The mobile phase used was an discriminating liquid (discriminating agent concentration 40 wt %) consisting of DPTFA-B-CD:n-paraffin SL (n-paraffin with a boiling point of 182~212° C. at atmospheric pressure, produced by Nippon Sekiyu Kagaku):diisopropyl ether (with a boiling point of 77° C. at atmospheric pressure, produced by Nippon Sekiyu Kagaku)=2:1:2 (by weight). DPTFA-B-CD functioned as an optically active discriminating agent, n-paraffin SL, as a diluent, and diisopropyl ether, as a diluent with desorbability.

(Adsorption separation process using simulated moving bed)

Figure 6:
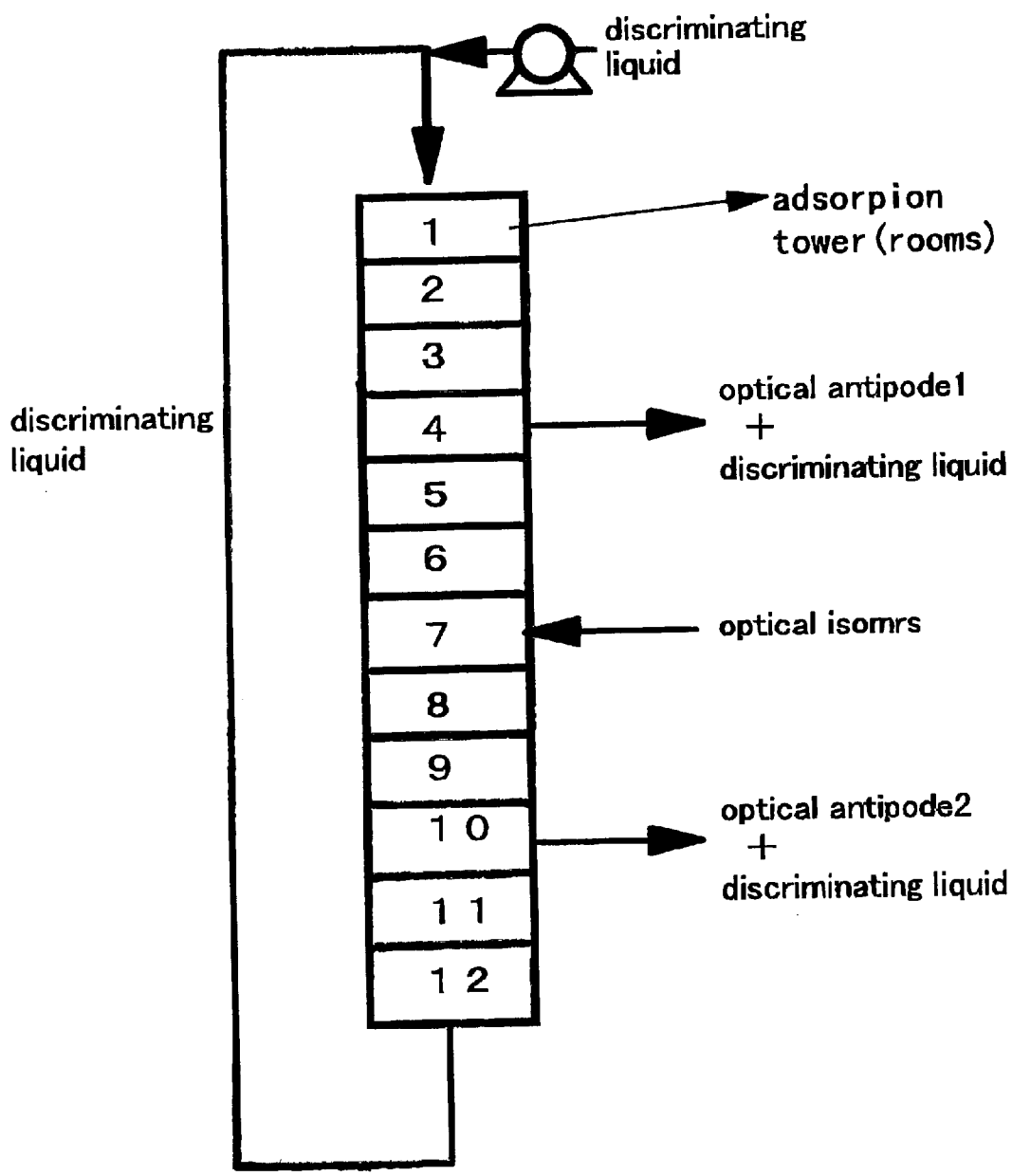
FIG. 6 shows a simulated moving bed apparatus as used in Example 10 herein.

Twelve 1 m long 4.75 mm inner dia. stainless steel columns were connected to be used for adsorption, and were packed with silica gel 4B (30~80-mesh, produced by Fuji Silicia). A simulated moving bed process as shown in FIG. 6 was used for confirmation according to the following method. The fluid outlet hole and inlet hole were controlled by using a rotary valve respectively.

The experiment was performed always at room temperature. From the inlet, a solution consisting of DPTFA-B-CD:n-paraffin SL:methyl RS-2-chloropropionate (produced by A. H. Marks)=2:1:1 was supplied at 2.32 ml/h. The discriminating liquid was supplied at 180.90 ml/h. The solution from the extract was taken out at 28.69 ml/h, and the solution from the raffinate, at 26.80 ml/h. The rotary valve was switched every 380 seconds. Operation was continued under these conditions for 12 hours till a steady state was reached. As a result, from the extract, methyl S-2-chloropropionate flowed out at 7800 ppm, and from the raffinate, methyl R-2-chloropropionate flowed out at 8100 ppm, respectively at 100% ee optical purity. The components were analyzed by gas chromatography using Chiraldex B-TA Capillary Column (produced by ASTEC).

The solution containing methyl S-2-chloropropionate taken out from the raffinate was distilled at a reduced pressure of 30 mm Hg by an evaporator, to obtain a solution consisting of isopropyl ether and methyl S-2-chloropropionate (boiling point of methyl S-2-chloropropionate at 30 mm Hg: about 50~60° C., boiling point of n-paraffin SL at 30 mm Hg: higher than 80° C.). Furthermore, isopropyl ether (boiling point at atmospheric pressure: 77° C.) was taken out by atmospheric distillation, to obtain methyl S-2-chloropropionate (boiling point at atmospheric pressure: 133° C.) with a chemical purity of 96% (optical purity of 100% ee) remaining at the tower bottom.

The bottom solution of the evaporator was concentrated further till methyl 2-chloropropionate content became almost zero, and isopropyl ether and n-paraffin SL were added to prepare a solution with the composition of the mobile phase, for returning it to the mobile phase.

It was confirmed that the optical isomers were efficiently separated by adsorption in a continuous process and that the discriminating liquid could be returned to the process system.

(Performance evaluation of cyclodextrin derivative compositions)

The following examples show the results of evaluation on discriminating liquids consisting of any of several cyclodextrin derivatives and a diluent.

The batch operation evaluation results in the following respective examples were obtained by measuring under static conditions. The batch operation evaluation can be regarded to simply evaluate the adsorption separability obtained by any other evaluation method such as the simulated moving bed method as described in Example 10. That is, if adsorption selectivity can be obtained under static conditions, a large difference can be found also by the simulated moving bed method. So, the optical isomers which can be differentiated under static conditions can be easily separated by chromatography using a substantial batch method or moving bed method.

EXAMPLE 11

1.0 gram of faujasite zeolite KY burned at 500° C. for 3 hours was weighed, and 3.5 g of a homogeneous solution consisting of 4.0 of DhxTFA-B-CD as discriminating agent, 6.0 g of p-diethylbenzene (produced by Toray) and 1.0 g of methyl RS-2-chloropropionate (produced by Tokyo Kasei) was added to it, for adsorption at room temperature for 24 hours. The R/S ratio of methyl RS-2-chloropropionate in the supernatant solution was analyzed by gas chromatography using a Chiraldex B-TA (produced by ASTEC) column. The result is shown in Table 1.

EXAMPLE 12

Adsorption separability was evaluated as described for Example 11, except that DOTFA-B-CD was used as the discriminating agent. The result is shown in Table 1.

EXAMPLE 13

Adsorption separability was evaluated as described for Example 11, except that DOAc-B-CD was used as the discriminating agent. The result is shown in Table 1.

EXAMPLE 14

Adsorption separability was evaluated as described for Example 11, except that DOPr-B-CD was used as the discriminating agent. The result is shown in Table 1.

EXAMPLE 15

Adsorption separability was evaluated as described for Example 11, except that DOBu-B-CD was used as the discriminating agent. The result is shown in Table 1.

EXAMPLE 16

Adsorption separability was evaluated as described for Example 11, except that DOVa-B-CD was used as the discriminating agent. The result is shown in Table 1.

EXAMPLE 17

Adsorption separability was evaluated as described for Example 11, except DOHx-B-CD was used as the discriminating agent. The result is shown in Table 1.

EXAMPLE 18

Adsorption separability was evaluated as described for Example 11, except DDTFA-B-CD was used as the discriminating agent. The result is shown in Table 1.

EXAMPLE 19

Adsorption separability was evaluated as described for Example 11, except DBuPr-B-CD was used as the discriminating agent. The result is shown in Table 1.

EXAMPLE 20

Adsorption separability was evaluated as described for Example 11, except DBuTFA-B-CD was used as the discriminating agent. The result is shown in Table 1.

TABLE 1

| Results of Example 11–20 | | |
|---|---|---|
| Example No. | discriminating agent | $\alpha$R/S |
| 11 | DHxTFA-B-CD | 1.72 |
| 12 | DOTFA-B-CD | 1.62 |
| 13 | DOAc-B-CD | 1.43 |
| 14 | DOPr-B-CD | 1.16 |
| 15 | DOBu-B-CD | 1.24 |
| 16 | DOVa-B-CD | 1.16 |
| 17 | DOHx-B-CD | 1.40 |
| 18 | DDTFA-B-CD | 1.53 |
| 19 | DBu-Pr-B-CD | 2.37 |
| 20 | DBuTFA-B-CD | 2.00 |

INDUSTRIAL AVAILABILITY

When the method for resolving optical isomers of the present invention is used, optical isomers can be efficiently resolved.

The optical antipodes obtained by using the optical resolution method can be used widely as various chemical products such as agricultural chemicals, drugs, food additives and their intermediates.

What is claimed is:

1. A method for resolving optical isomers, in which a discriminating liquid, comprising a discriminating agent (A) having optical activity comprising at least two asymmetric atoms capable of discriminating said optical isomers wherein said discriminating agent is at least one selected from the group consisting of saccharides, hydroxycarboxylic acids, saccharide derivatives, tartaric acid, tartaric acid derivatives, crown ethers, binaphtol and hydroxycarboxylic acid derivatives, and a diluent (B) which is capable of dissolving said discriminating agent, is provided the steps comprising bringing said discriminating liquid into contact with a mixture containing said optical isomers in countercurrent flow, to thereby resolve said optical isomers by adsorption separation, distillation separation, absorption separation or membrane separation, and wherein said discriminating liquid is recycled at an optical isomer content of 5 wt % or less, and wherein one or more of the following conditions is further present and performed in the conduct of said method:

(a) the dielectric constant of the diluent is 30 or less and the viscosity of the discriminating liquid is 0.2 Pa·s or less at the temperature of the resolving operation;

(b) said discriminating agent must have the property of splitting the $^1$H or $^{13}$C-NMR spectrum peak of the optical isomers, and said diluent has a dielectric constant that is equal to or lower than the dielectric constant of the measuring solvent at the time of measuring the $^1$H or $^{13}$C-NMR spectrum;

(c) the boiling point of at least one component of said discriminating agent, at the pressure of said resolving step, is higher than the boiling point of at least one component of said diluent at the pressure of said resolving step;

(d) the boiling point of at least one compound of said diluent at the pressure of said resolving step is higher, by 10° C. or more, than the boiling point of said optical isomers to be resolved, at the pressure of said resolving step; and (e) the concentration of said discriminating agent in said discriminating liquid is 10 wt % or more.

2. A method for resolving optical isomers, according to claim 1, wherein said discriminating agent is cyclodextrin derivative.

3. A method for resolving optical isomers, according to claim 2, wherein said cyclodextrin derivative comprises ether groups and/or ester groups.

4. A method for resolving optical isomers, according to claim 1, wherein an optical antipode having enhanced optical purity is separated from the discriminating liquid by distillation and/or evaporation.

5. A method for resolving optical isomers, according to claim 1, wherein an optical antipode having enhanced optical purity is separated from the discriminating liquid by distillation under reduced pressure and/or evaporation under reduced pressure.

6. A method for resolving optical isomers, according to claim 1, wherein one of the optically resolved optical antipodes is subsequently racemized and recycled as optical isomers.

7. A method for resolving optical isomers, according to claim 1, wherein the distillation separation or absorption separation of said optical isomers is effected under conditions not precipitating crystals.

8. A method for resolving optical isomers, according to claim 7, wherein said discriminating liquid is injected into an upper stage of a distillation tower or absorption tower while an optical isomer mixture is injected into a middle stage of said distillation tower or said absorption tower.

9. A method for resolving optical isomers, according to claim 7, wherein said optical isomers and said discriminating liquid are injected into a middle stage of a distillation tower or absorption tower.

10. A method for resolving optical isomers, according to claim 7, wherein a solution containing said discriminating liquid and an optical antipode is removed from a lower stage of a distillation tower, and wherein said discriminating liquid is subsequently separated from said optical antipode and returned to the distillation tower.

11. A method for resolving optical isomers, according to claim 7, wherein a solution containing an optical antipode is removed from an upper stage or lower stage of a distillation tower or absorption tower, and wherein the recovered optical antipode is racemized and returned to said distillation tower or said absorption tower.

12. A method for resolving optical isomers, according to claim 7, which is carried out under reduced pressure less than atmospheric pressure.

13. A method for resolving optical isomers, according to claim 7, wherein the tower bottom temperature of said distillation tower is 40 to 200° C.

14. A method for resolving optical isomers, according to claim 1, wherein, when said optical isomers are resolved by adsorption separation, the adsorption selection coefficient $\alpha_{C/B}$ of one optical antipode, (C) of said optical isomers to said diluent (B), is 0.2 to 5.0.

15. A method for resolving optical isomers, according to claim 1 or 14, which is carried out using a simulated moving bed.

16. The method defined in claim 1, wherein said discriminating liquid comprises a component in which asymmetric atoms are adjacently bonded to each other.

17. The method defined in claim 1, wherein both of conditions (a) and (b) are present.

18. The method defined in claim 1, wherein all of conditions (a), (b) and (c) are present.

19. The method defined in claim 1, wherein all of the conditions (a), (b), (c), (d) and (e) are present.

20. The method defined in claim 1, wherein the conditions of (a) and (c) are present.

21. The method defined in claim 1, wherein all of the conditions of (a), (c) and (d) are present.

22. The method defined in claim 1, wherein the components of the resolution have the following boiling point relationship: the boiling point of a component of said discriminating agent>boiling point of a component of said diluent>boiling point of optical isomers+10° C.

23. A method for resolving optical isomers in which a discriminating liquid, comprising a discriminating agent (A) comprising at least two asymmetric atoms capable of discriminating said optical isomers, and a diluent (B) which is capable of dissolving said discriminating agent, is brought into contact with a mixture containing said optical isomers in countercurrent flow, to resolve said optical isomers by adsorption separation, distillation separation, or absorption separation or membrane separation, and wherein said discriminating liquid is recycled at an optical isomer content of 5 wt % or less, and wherein one or more of the following conditions is further present and performed in the conduct of said method:

the dielectric constant of the diluent is 30 or less and the viscosity of the discriminating liquid is 0.2 Pa·s or less at the temperature of the resolving operation;

said discriminating agent splits the $^1$H or $^{13}$C-NMR spectrum peak of the optical isomers, and said diluent has a dielectric constant equal to or lower than the dielectric constant of the measuring solvent at the time of measuring the $^1$H or $^{13}$C-NMR spectrum;

the boiling point of at least one component of said discriminating agent, at the pressure of said resolving step, is higher than the boiling point of at least one component of said diluent at the pressure of said resolving step;

the boiling point of at least one compound of said diluent at the pressure of said resolving step is higher by 10° C. or more than the boiling point of said optical isomers to be resolved, at the pressure of said resolving step; and the concentration of said discriminating agent in said discriminating liquid is 10 wt % or more, wherein said discriminating agent is a cyclodextrin derivative comprising a compound represented by the following formula (I):

(I)

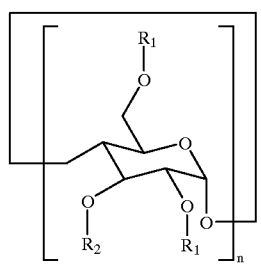

where n=6–8, with the proviso that when R1 denotes n-hexyl, R2 denotes trifluoroacetyl; that when R1 denotes n-octyl, R2 denotes trifluoroacetyl, acetyl, propionyl, butyryl, valeryl, or hexanoyl; that when R1 denotes n-decyl, R2 denotes trifluoroacetyl; and that when R1 denotes n-butyl, R2 denotes propionyl or trifluoroacetyl.

24. A method for resolving optical isomers in which a discriminating liquid, comprising a discriminating agent (A) comprising at least two asymmetric atoms capable of discriminating said optical isomers, and a diluent (B) which is capable of dissolving said discriminating agent, is brought into contact with a mixture containing said optical isomers in countercurrent flow, to resolve said optical isomers by adsorption separation, distillation separation, or absorption separation or membrane separation, and wherein said discriminating liquid is recycled at an optical isomer content of 5 wt % or less, and wherein one or more of the following conditions is further present and performed in the conduct of said method:

the dielectric constant of the diluent is 30 or less and the viscosity of the discriminating liquid is 0.2 Pa·s or less at the temperature of the resolving operation;

said discriminating agent splits the $^1$H or $^{13}$C-NMR spectrum peak of the optical isomers, and said diluent has a dielectric constant equal to or lower than the dielectric constant of the measuring solvent at the time of measuring the $^1$H or $^{13}$C-NMR spectrum the boiling point of at least one component of said discriminating agent, at the pressure of said resolving step, is higher than the boiling point of at least one component of said diluent at the pressure of said resolving step;

the boiling point of at least one compound of said diluent at the pressure of said resolving step is higher by 10° C. or more than the boiling point of said optical isomers to be resolved, at the pressure of said resolving step; and the concentration of said discriminating agent in said discriminating liquid is 10 wt % or more, wherein said discriminating liquid comprises hydrophobic derivative of a cyclodextrin.

25. A method for resolving optical isomers, in which a discriminating liquid, comprising a discriminating agent (A) which is a cyclodextrin derivative represented by the following formula (I):

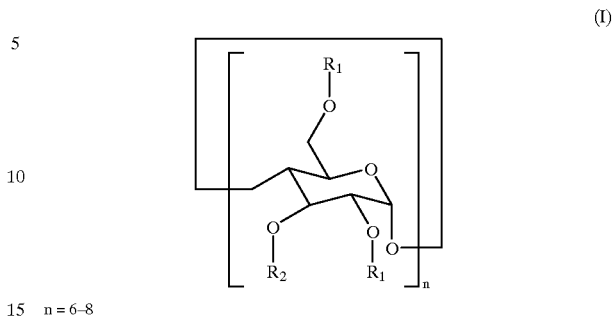

n = 6–8 with the proviso that when $R_1$ denotes n-hexyl, $R_2$ denotes trifluoroacetyl; that when $R_1$ denotes n-octyl, $R_2$ denotes trifluoroacetyl, acetyl, propionyl, butyryl, valeryl or hexanoyl; that when $R_1$ denotes n-decyl, $R_2$ denotes trifluoroacetyl; and that when $R_1$ denotes n-butyl, $R_2$ denotes propionyl or trifluoroacetyl;

and a diluent (B), is brought into contact with a mixture containing said optical isomers in countercurrent flow, to resolve said optical isomers by adsorption separation, distillation separation, adsorption separation or membrane separation.

26. A method for resolving optical isomers, in which a discriminating liquid, comprising a discriminating agent (A) comprising at least two or more asymmetric atoms capable of discriminating said optical isomers, and a diluent (B) which is capable of dissolving said discriminating agent, is brought into contact with a mixture containing said optical isomers in countercurrent flow, to resolve said optical isomers by adsorption separation, distillation separation, absorption separation or membrane separation, and wherein said discriminating liquid is recycled at an optical isomer content of 5 wt % or less, and wherein the dielectric constant of the diluent is 30 or less and the viscosity of the discriminating liquid is 0.2 Pa·s or less at the temperature of the resolving operation.

27. A method for resolving optical isomers, in which a discriminating liquid, comprising a discriminating agent (A) comprising at least two or more asymmetric atoms capable of discriminating said optical isomers, and a diluent (B) which is capable of dissolving said discriminating agent, is brought into contact with a mixture containing said optical isomers in countercurrent flow, to resolve said optical isomers by adsorption separation, distillation separation, absorption separation or membrane separation, and wherein said discriminating liquid is recycled at an optical isomer content of 5 wt % or less, and wherein the boiling point of at least one compound of said diluent at the pressure of said resolving step is higher, by 10° C. or more than the boiling point of said optical isomers to be resolved, at the pressure of said resolving step.

* * * * *

UNITED STATES PATENT AND TRADEMARK OFFICE
CERTIFICATE OF CORRECTION

PATENT NO. : 6,379,552 B1
DATED : April 30, 2002
INVENTOR(S) : Kitagawa et al.

It is certified that error appears in the above-identified patent and that said Letters Patent is hereby corrected as shown below:

Column 4,
Line 43, please change "discriminating agent" to -- term "discriminating agent" --;
Line 45, please delete "of" after "antipode".

Column 7,
Line 31, please delete "with" after "compound".

Column 8,
Line 56, please delete "to" after "inhibited,".

Column 13,
Line 23, please delete "in" after "higher"; and
Line 66, please delete "p" after "economical." and have "Furthermore, it is" begin a new paragraph.

Column 17,
Line 23, please change "3:3" to -- 3:1 --.

Column 22,
Line 32, please change "$_1H$" to -- $^1H$ --.

Signed and Sealed this

Twenty-fourth Day of September, 2002

*Attest:*

JAMES E. ROGAN
*Attesting Officer*     *Director of the United States Patent and Trademark Office*